United States Patent [19]
Alfano et al.

[11] Patent Number: 5,656,810
[45] Date of Patent: Aug. 12, 1997

[54] METHOD AND APPARATUS FOR EVALUATING THE COMPOSITION OF AN OIL SAMPLE

[75] Inventors: Robert R. Alfano, Bronx; Cheng H. Liu, Flushing, both of N.Y.

[73] Assignee: The Research Foundation of City College of New York

[21] Appl. No.: 155,450

[22] Filed: Nov. 22, 1993

[51] Int. Cl.$^6$ .................................................. G01N 21/64
[52] U.S. Cl. ...................... 250/301; 250/255; 250/461.1
[58] Field of Search ............................ 250/301, 339.12, 250/461.1, 255; 356/70

[56] References Cited

U.S. PATENT DOCUMENTS

| | | | |
|---|---|---|---|
| 3,462,596 | 8/1969 | Saunders | 250/343 |
| 4,473,651 | 9/1984 | Goldstein | 356/70 |
| 4,609,821 | 9/1986 | Summers | 250/301 |
| 4,814,614 | 3/1989 | Tsui | 250/301 |
| 4,920,792 | 5/1990 | Di Foggio | 73/153 |
| 4,990,773 | 2/1991 | Supernaw et al. | 250/255 |
| 5,049,738 | 9/1991 | Gergely et al. | 250/461.1 |
| 5,145,785 | 9/1992 | Maggard et al. | 250/301 |
| 5,381,002 | 1/1995 | Morrow et al. | 250/461.1 |

FOREIGN PATENT DOCUMENTS

| | | | |
|---|---|---|---|
| 1015287 | 4/1983 | U.S.S.R. | 250/301 |
| 1594391 | 9/1990 | U.S.S.R. | 376/70 |
| 2248844 | 10/1990 | U.S.S.R. | 356/70 |
| 2217838 | 11/1989 | United Kingdom | 250/339.09 |

OTHER PUBLICATIONS

Brownrigg et al, "Low Temperature Total Luminescence Contour Spectra of Six Topped Crude Oils and Their Vacuum Distrillate and Residuum Fractions", U.S. Dept. of Energy, BETC/R1-78/13, Aug. 1978.

*Primary Examiner*—Carolyn E. Fields
*Attorney, Agent, or Firm*—Kriegsman & Kriegsman

[57] ABSTRACT

A method and apparatus for evaluating the composition of an oil sample. The method and apparatus are premised on the discovery that spectral differences can be observed in the luminescence, excitation, light scattering and absorption spectra in the near UV, visible and near IR regions for various crude oil components, such as asphaltenes, deasphalted crude oil and organic solid residues. Accordingly, in one preferred embodiment the method comprises illuminating an oil sample with light of a suitable excitation wavelength, measuring the resultant fluorescence therefrom and comparing the resultant fluorescence to appropriate standards derived from known components of crude oil.

1 Claim, 27 Drawing Sheets

METHOD AND APPARATUS FOR EVALUATING THE COMPOSITION OF AN OIL SAMPLE

BACKGROUND OF THE INVENTION

The present invention relates generally to methods and apparatuses for evaluating the composition of an oil sample and more particularly to a method and apparatus for evaluating the composition of an oil sample using optical spectroscopy.

As can readily be appreciated, it is very desirable for those persons in the oil industry to be able to evaluate the composition of an oil sample. For example, one may want to know the composition of a crude oil sample since certain components of crude oil, such as asphaltenes and paraffins, negatively affect crude oil quality. In the past, the composition of crude oil samples have typically been determined chemically, e.g., by using various chromatography techniques.

The ability to measure crude oil "instability," that is, the tendency for solid particles to precipitate from their host fluids, has considerable economic value. The solids in question are essentially asphaltenes, high molecular weight polynuclear aromatic hydrocarbons, which have limited solubility in the crude oil despite its being also of hydrocarbon composition. Often, they do not exist in true solution but, instead, in finely divided particulate or colloidal suspension.

Such metastable states are disturbed by lifting and pumping and by comingling with other substances or reagents. For example, it is known that gas lifting, that is, the forcing of oil from its formation by compressed gas, can cause precipitation. Also, carbon dioxide, a polar gas, is more troublesome than, say, methane which is the major component of natural gas.

These precipitates build up and coat and clog well shafts, pipelines and storage vessels. Remedies include chipping, sandblasting and heating, all labor intensive and costing downtime. So-called heavy crudes have higher asphaltene content, but factors affecting instability are often subtle and discovered only empirically.

Polyaromatic structures have characteristic fluorescence. Hence, sampling and analysis on-site in real time could allow field personnel to adjust operating conditions to minimize the effects of this instability.

In U.S. Pat. No. 5,131,398 to Alfano et at., which issued Jul. 21, 1992 and which is incorporated herein by reference, there is disclosed a method and apparatus for distinguishing cancerous tumors and tissue from benign tumors and tissue or normal tissue using native fluorescence. The tissue to be examined is excited with a beam of monochromatic light at 300 nanometers (nm). The intensity of the native fluorescence emitted from tissue is measured at 340 and 440 nm. The ratio of the two intensities is then calculated and used as a basis for determining if the tissue is cancerous as opposed to benign or normal. The invention is based on the discovery that when tissue is excited, for example, with monochromatic light at 300 nm, the native fluorescence spectrum over the region from about 320 nm to 600 nm for cancerous tissue is substantially different from that for tissue that is either benign or normal. The technique is useful in both in vivo and in vitro testing of human as well as animal tissue.

SUMMARY OF THE INVENTION

It is an object of the present invention to provide a new and novel method and apparatus for evaluating the composition of an oil sample.

Additional objects of the invention, as well as features and advantages thereof, will be set forth in part in the description which follows, and in part will be obvious from the description or may be learned by practice of the invention. The objects of the invention also may be realized and attained by means of instrumentalities and combinations particularly pointed out in the appended claims.

The present invention is premised on the discovery that spectral differences can be observed in the luminescence, excitation, light scattering and absorption spectra in the uv, visible and near IR regions for various crude oil components, such as asphaltenes, deasphalted crude oil and organic solid residues. Accordingly, using optical spectroscopy, one can examine an oil sample for the presence of the aforementioned components.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In the drawings wherein like reference numerals represent like parts.

DETAILED DESCRIPTION OF PREFERRED EMBODIMENTS

As noted above, the present invention is premised on the fact that certain components of crude oil, such as asphaltenes, deasphalted crude oil and organic solid residues, exhibit differences in their respective luminescence, excitation, light scattering and absorption spectra in the near IR, near UV and visible regions. Accordingly, one can use these differences to examine an oil sample for the presence of the aforementioned components.

The foregoing principles were demonstrated on a plurality of oil samples obtained as follows: Sample Nos. 1 and 4 were crude oil samples taken from different wells. A portion of Sample No. 4 was treated with pentane until a precipitate formed and passed through filter paper, the collected precipitate (i.e. asphaltenes) being designated Sample No. 5 and the supernatant (i.e. deasphalted crude oil) being designated Sample No. 6. Sample No. 5 constituted about 3.9%, by weight, of the pentane-treated portion of Sample No. 4 whereas Sample No. 6 constituted about 96%, by weight, of the pentane-treated portion of Sample No. 4. A quantity of organic solid residues (e.g., paraffins) deposited on the surface of oil well pipes used in oil production was designated Sample No. 7.

Figure 1:
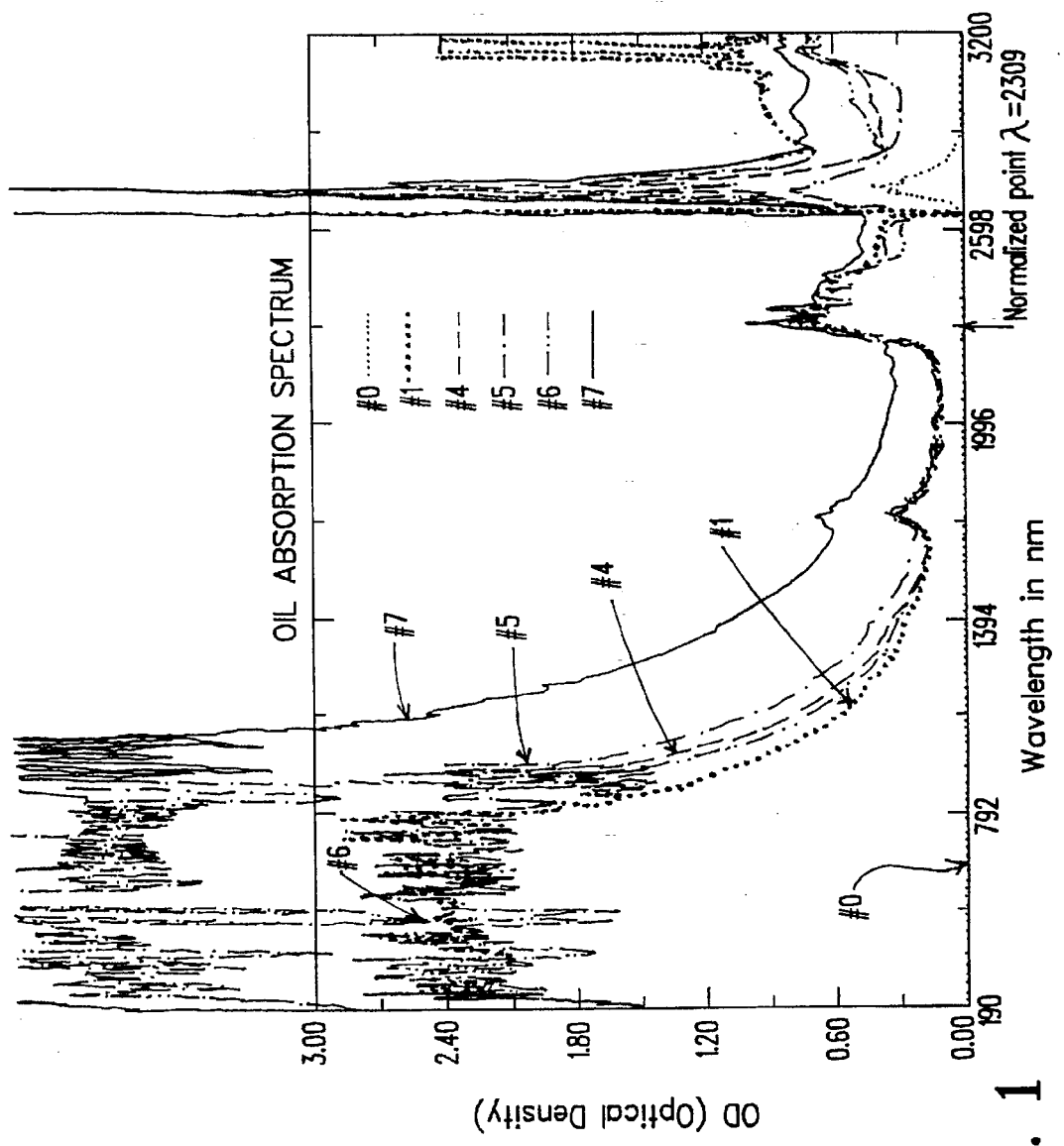
FIGS. 1 through 3 are graphs depicting the absorption spectra of various crude oil and crude oil components, the spectra of FIGS. 1 and 2 being normalized at 2.309 microns.
Figure 2:
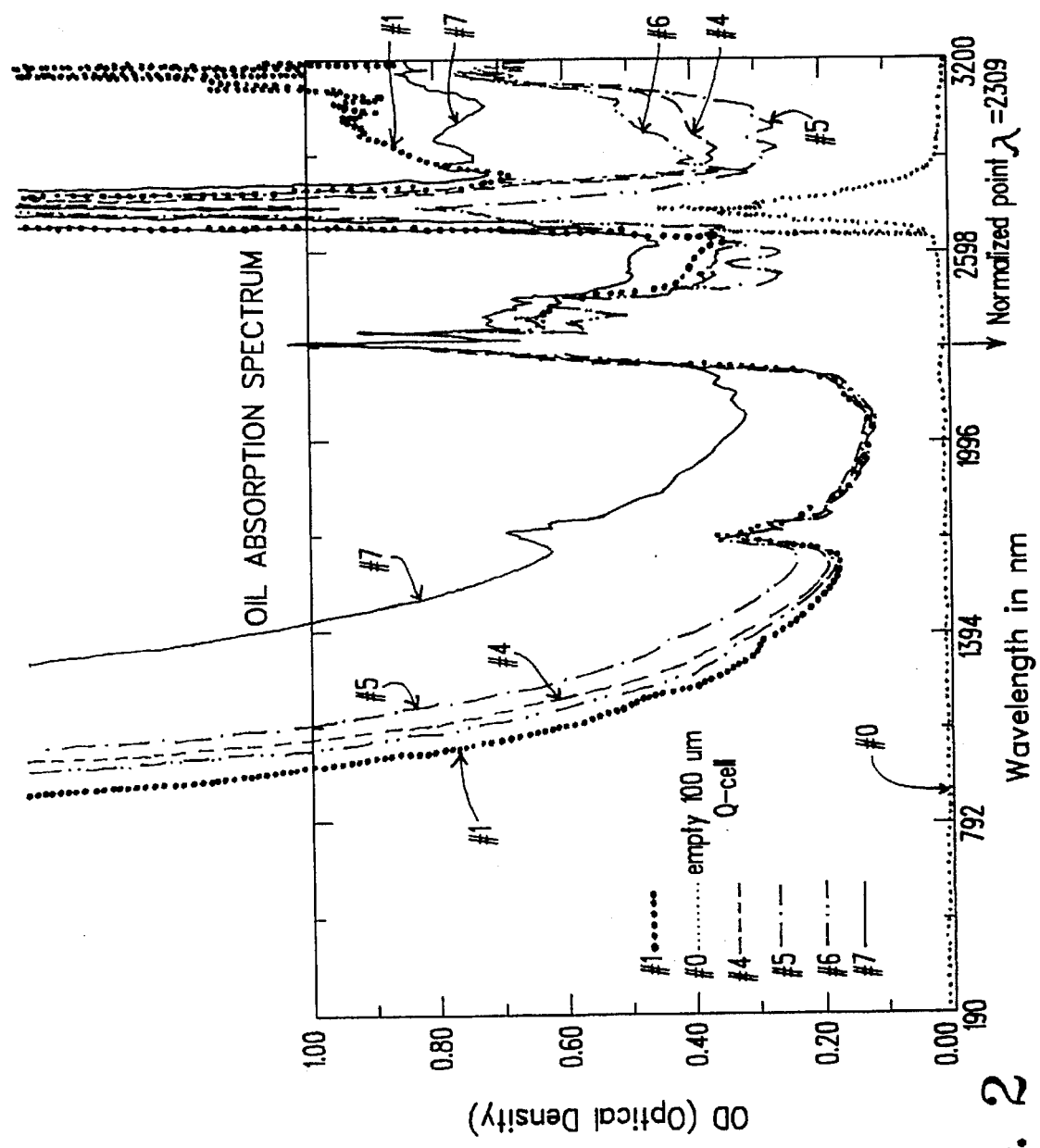
Figure 3:
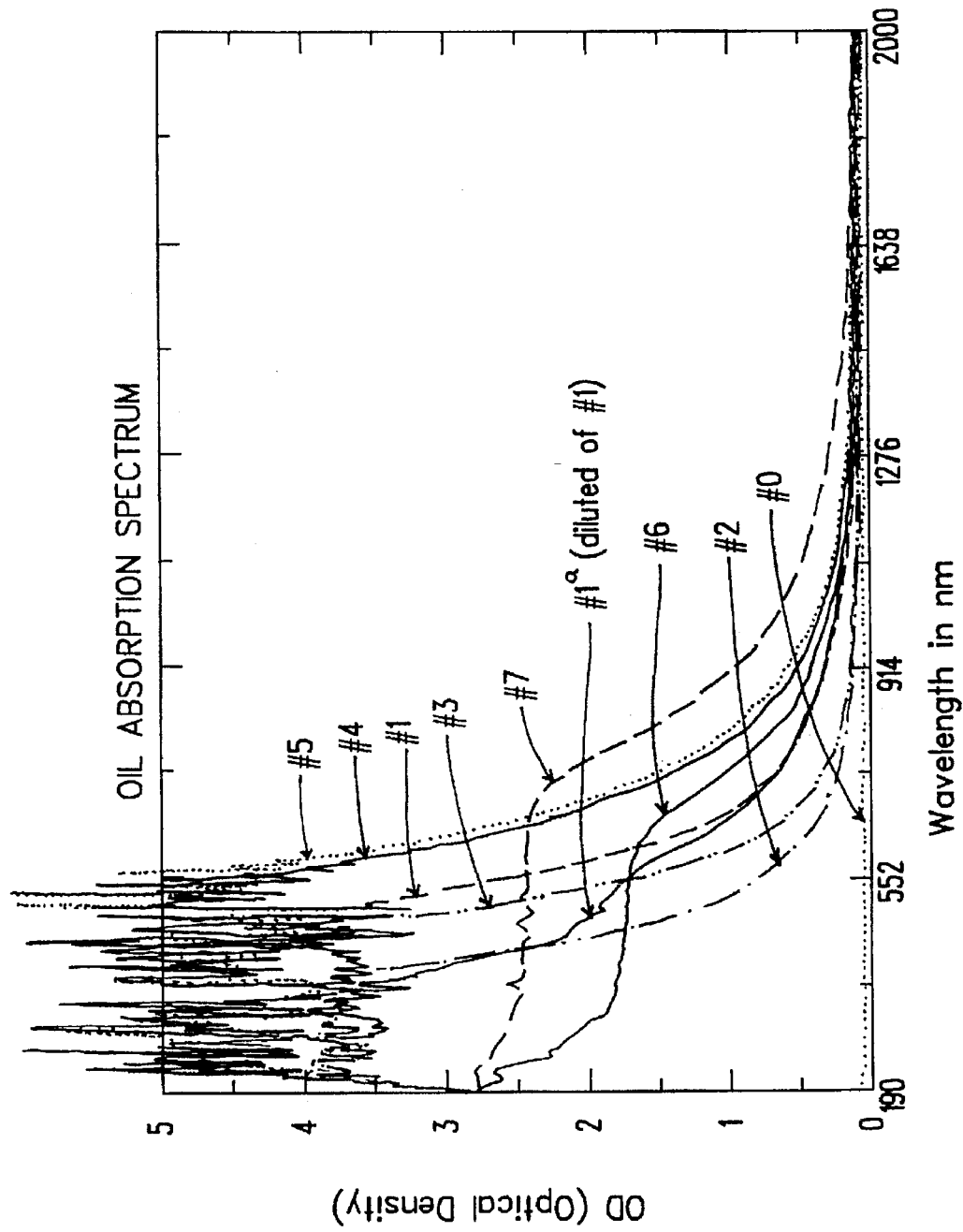

Referring now to FIGS. 1 through 3, there are shown the absorption spectra in the near UV, visible and near IR for Sample Nos. 1, 4, 5, 6 and 7 (Sample No. 0 being an empty sample holder serving as a control). As can be seen, there are significant absorption differences among the various types of samples which could permit one of ordinary skill in the art to determine the different components of an unknown oil sample. More specifically, it is noted that great variation among the types of samples occurs in the 3.0 μm, 1.3 μm, 1.65 μm and 2.4 μm regions. For example, as can be seen best in FIG. 2, the paraffin-containing sample, Sample No. 7, absorbs the most in the 2.4 μm region whereas the asphaltene-containing sample, Sample No. 5, absorbs the least in the same region. In fact, Sample No. 7 absorbs the most throughout the entire spectral region when normalized to the 2.309 micron band. There is a long wing extending from the visible region, probably due to scattering from particles.

The absorption spectra from 190 nm to 2000 nm (see FIG. 3) for the various samples also show differences. The main absorption from oils in the visible region appears to be due to asphaltenes in Sample No. 5 as can be seen by comparing the absorption of the crude oil sample of Sample No. 4. The deasphalted oil sample (Sample No. 6) appears to show less absorption and saturates in the visible spectrum below about 600 nm. Sample No. 7 shows a similar response to Sample No. 6. These spectra profiles are dependent on dilution with solvents indicating the role of precipitates (see Sample Nos. 1 and 1a in FIG. 3).

Figure 4:
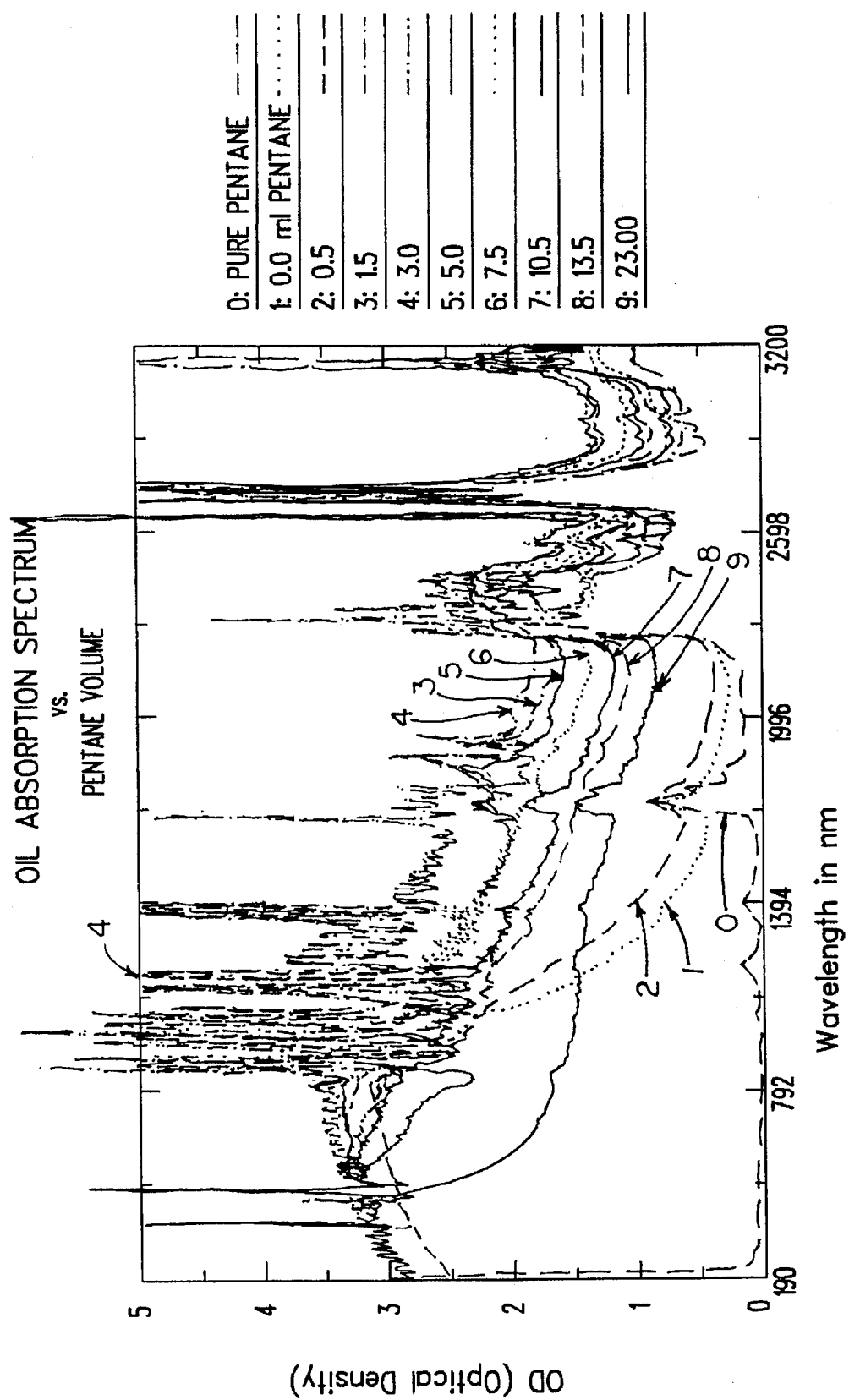
FIGS. 4 and 5 are graphs depicting the absorption spectra of various crude oil samples diluted with different amounts of pentane, the spectra being normalized at 2.309 microns.
Figure 5:
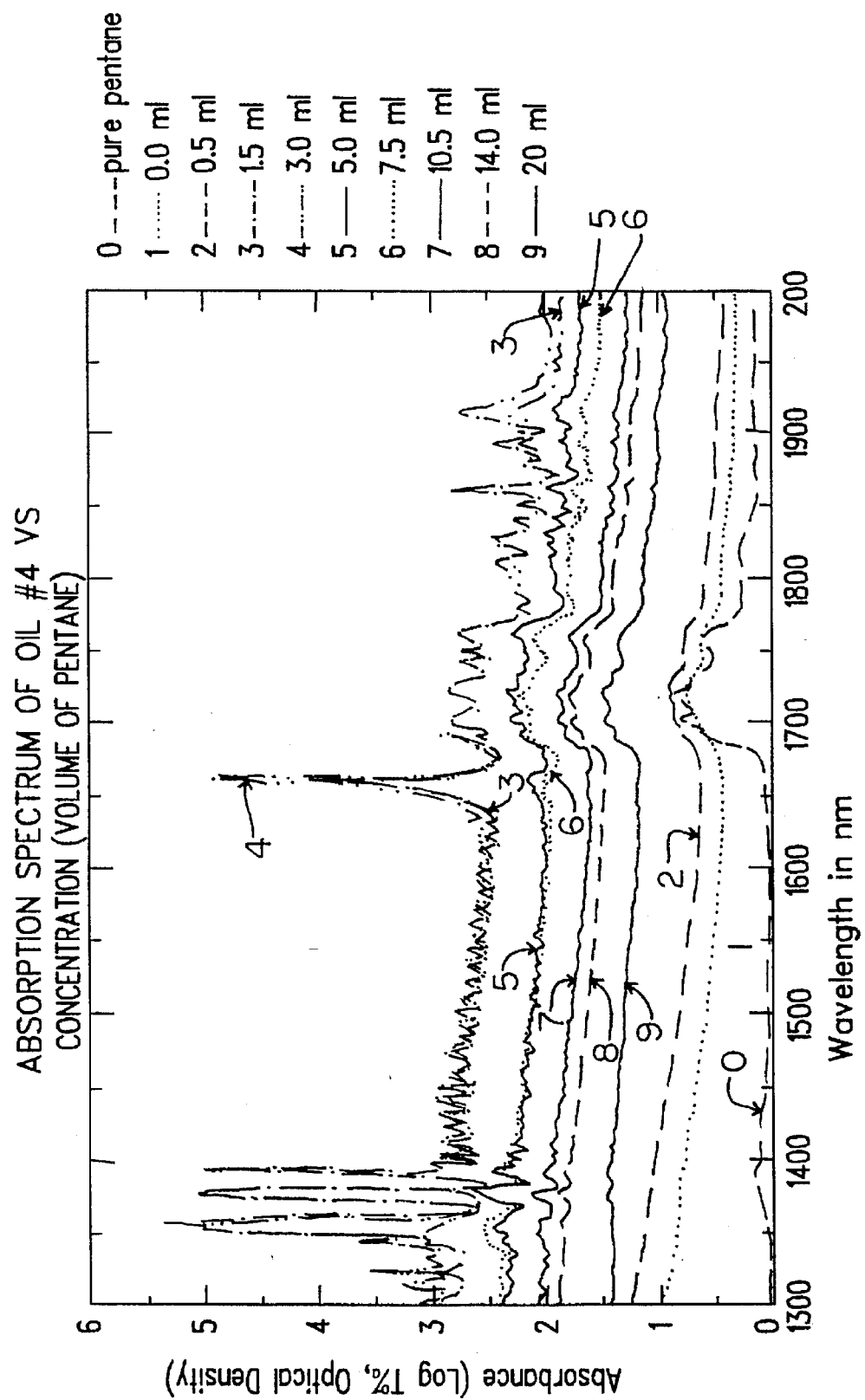
Figure 6A:
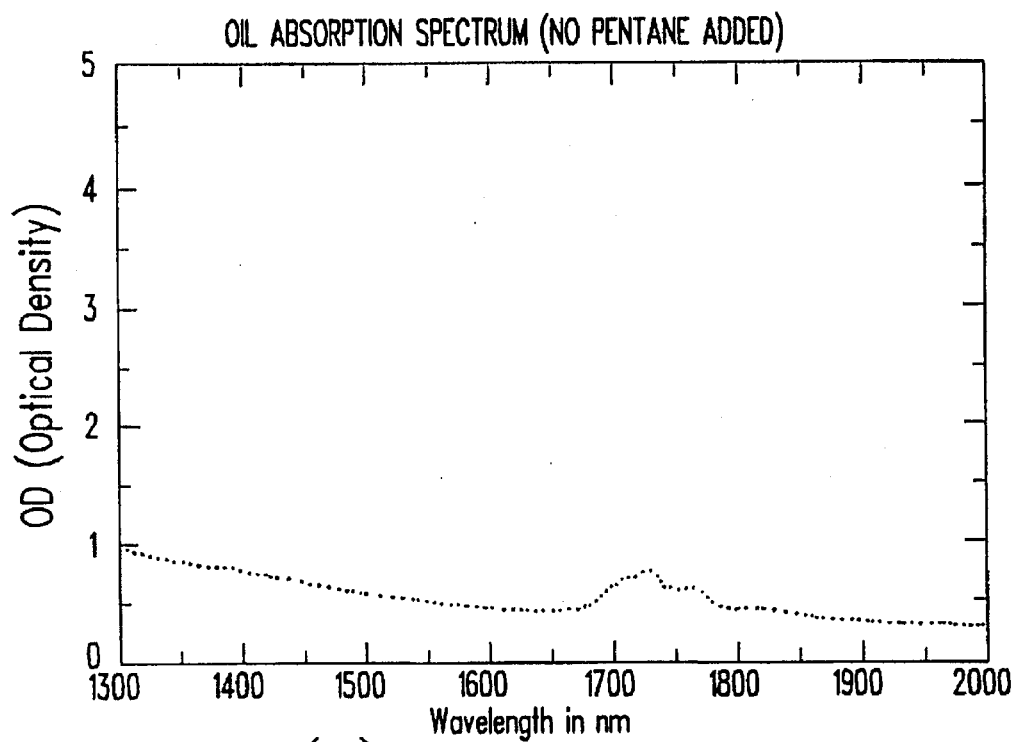
FIGS. 6(a) through 6(d) are graphs depicting certain individual absorption spectra shown together in FIG. 5.
Figure 6B:
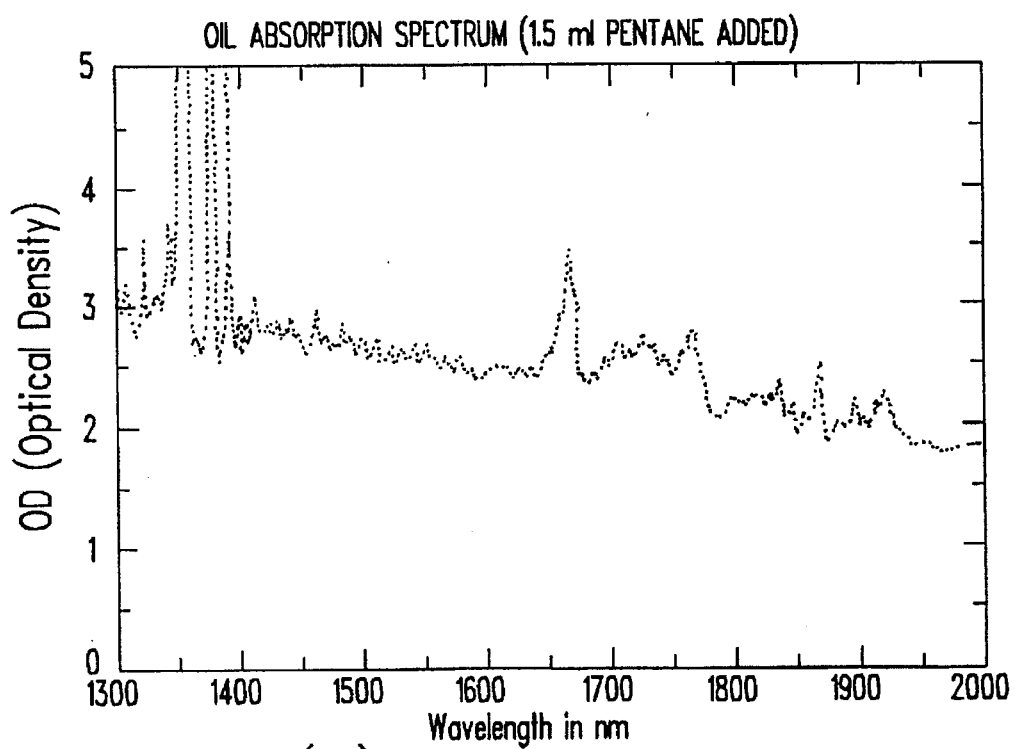
Figure 6C:
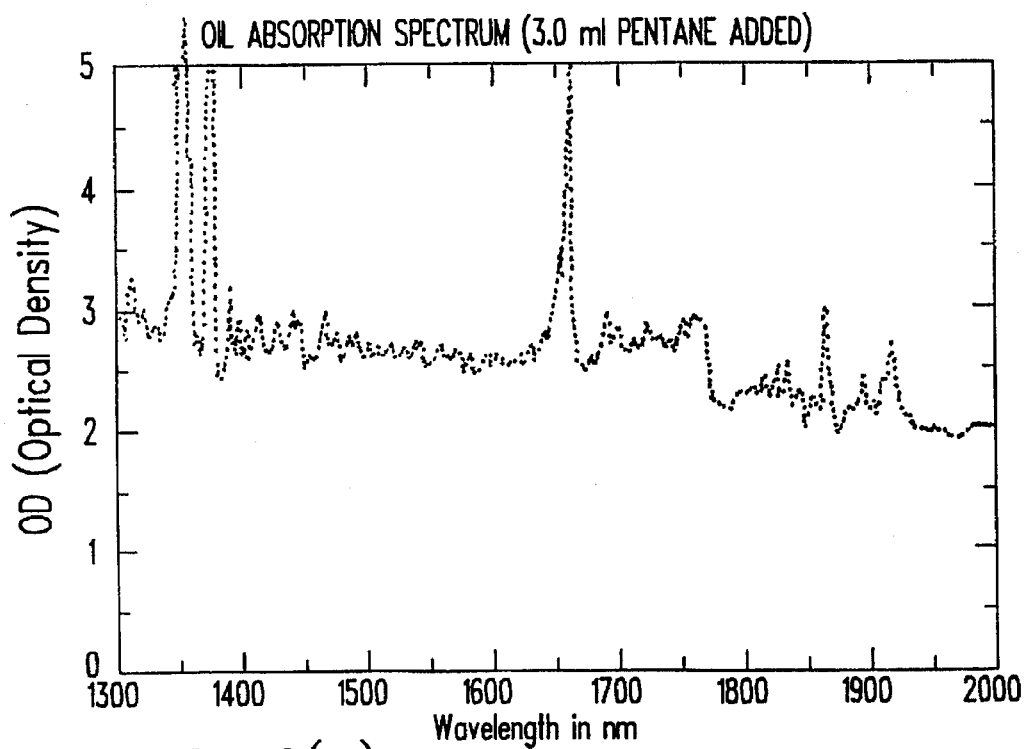
Figure 6D:
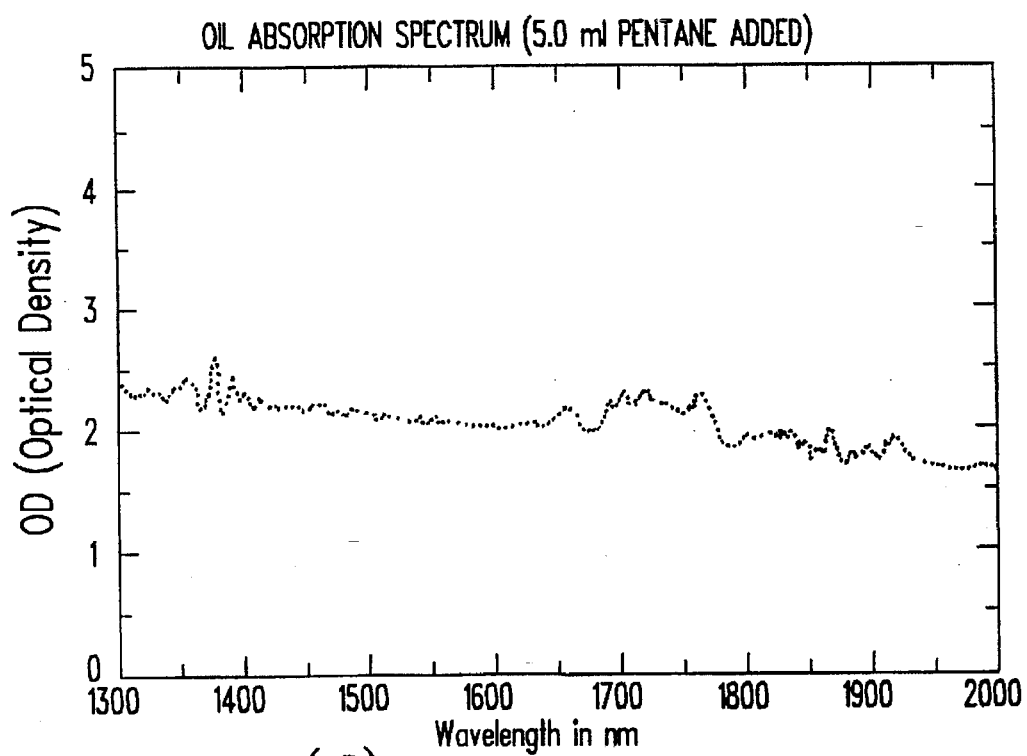
Figure 7A:
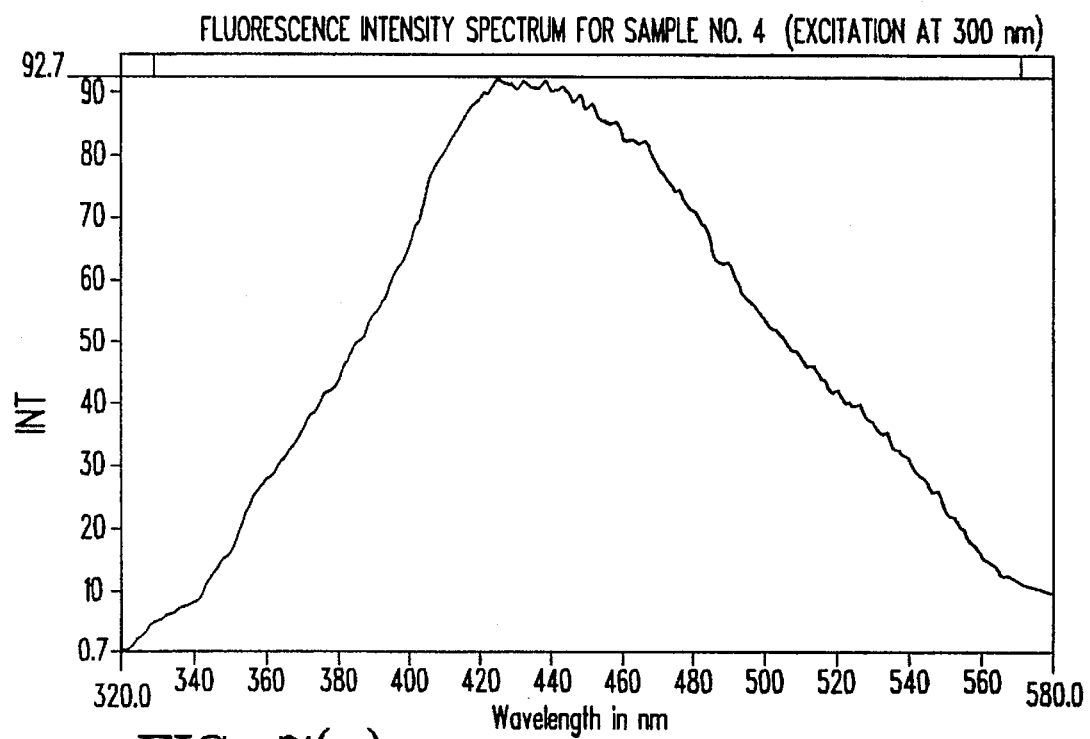
FIGS. 7(a) through 7(e) are graphs depicting the emission (i.e., fluorescence) spectra of various crude oil and crude oil component samples excited at 300 nm.
Figure 7B:
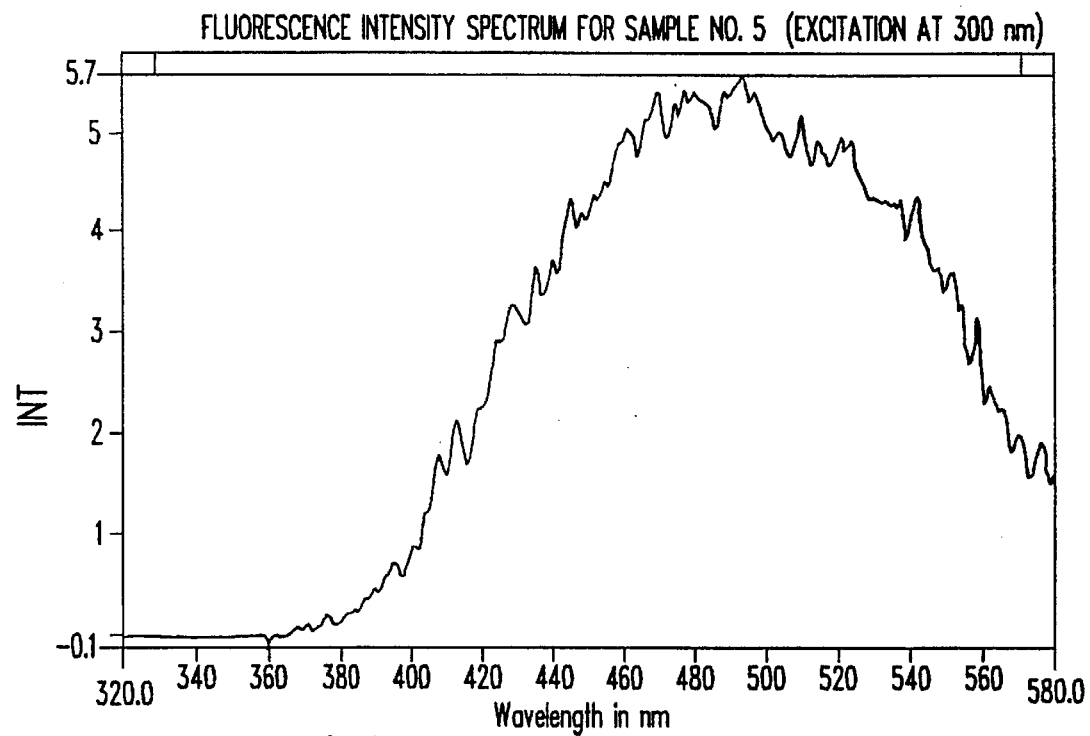
Figure 7C:
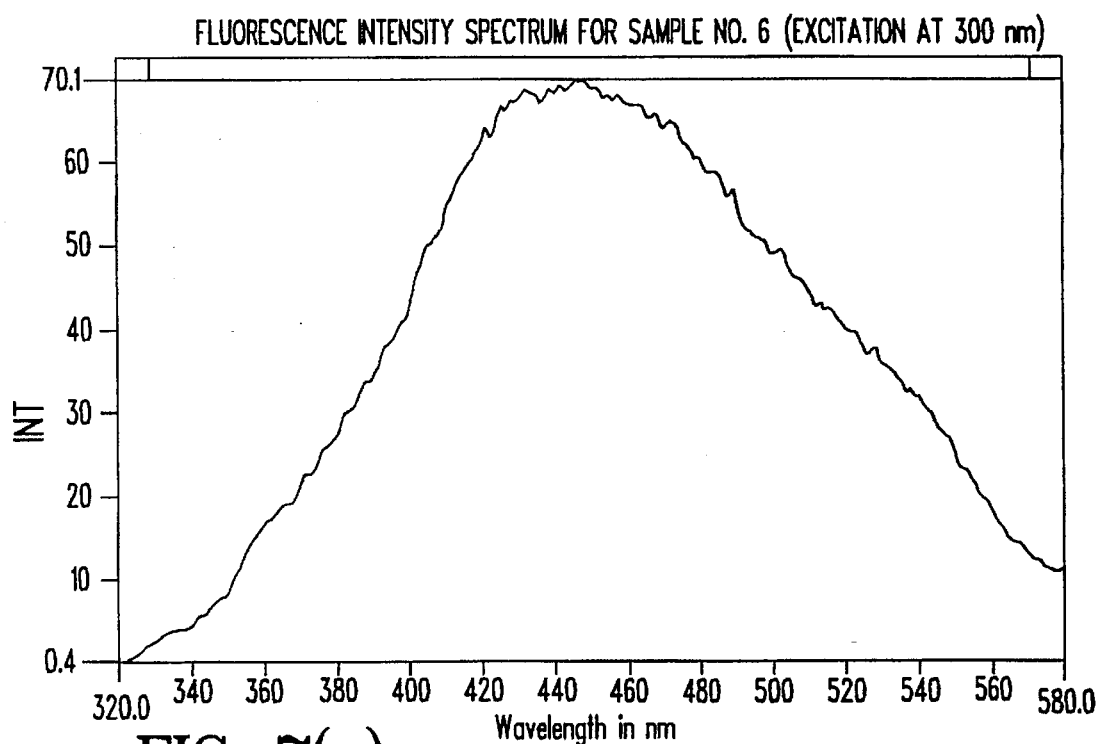
Figure 7D:
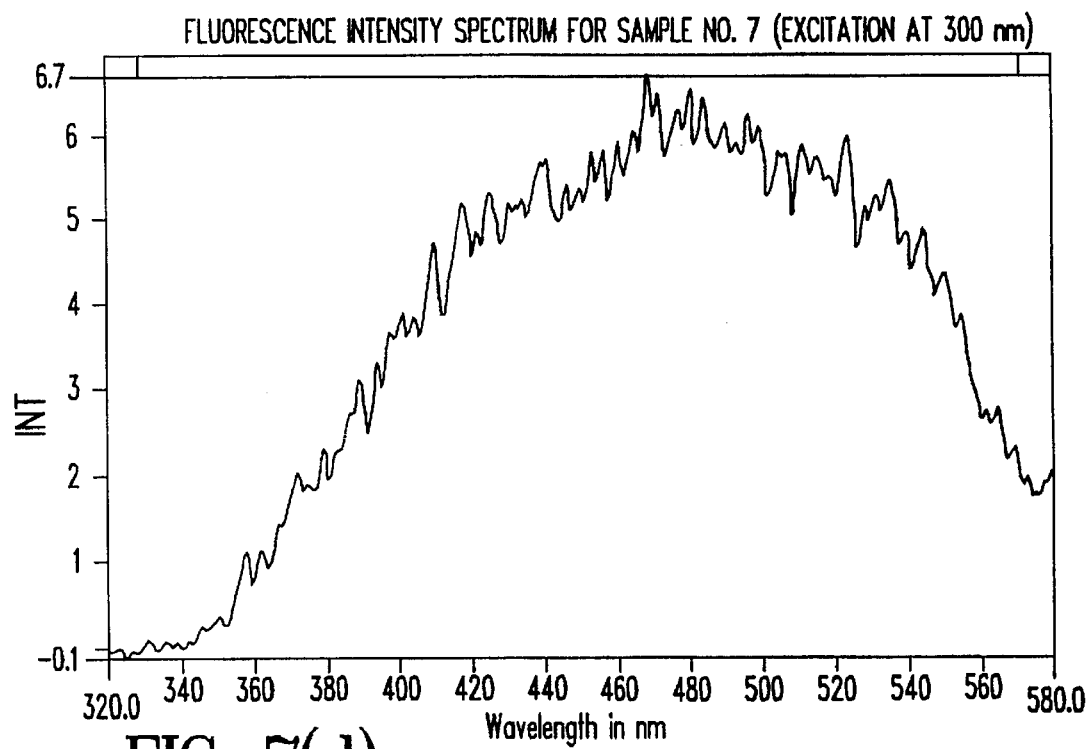
Figure 7E:
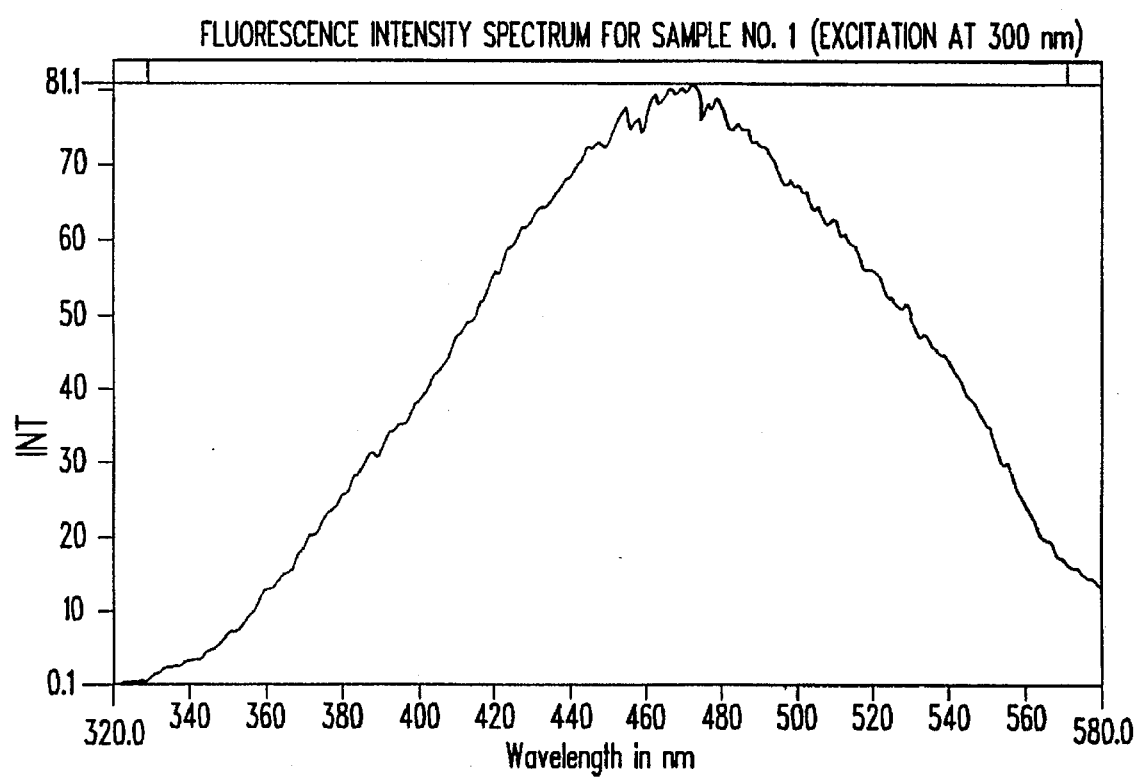

Referring now to FIGS. 4 and 5, there are shown the absorption spectra obtained when varying amounts of pentane were added to quantities of Sample No. 4. As can be seen, when the samples were diluted with pentane, the spectra showed an onset of sharp absorption lines between 1.3 to 1.4 μm and 1.6 to 1.8 μm (see FIG. 5). Selected individual curves from FIG. 5 are shown in FIGS. 6(a) through 6(d). Easily observable changes in the absorption spectra can be seen when 1 ml of Sample No. 4 was diluted with 1.5 ml of pentane. When the concentration of pentane was increased to over 5 ml, the effect on the absorption spectrum was reduced. The absorption background spanning the entire region showed an increase followed by a decrease as penme concentration was increased (see FIG. 5). As the concentration of pentane was added, asphaltene was precipitated out of the oil causing dramatic changes in the absorption spectra. The onset of changes are caused by increased absorption over a wide spectra wavelength range and an onset of many sharp spectral lines in a well defined wavelength range of 1.3 to 1.4 μm, 1.6 to 1.8 μm and 0.8 to 1.0 μm.

Figure 8:
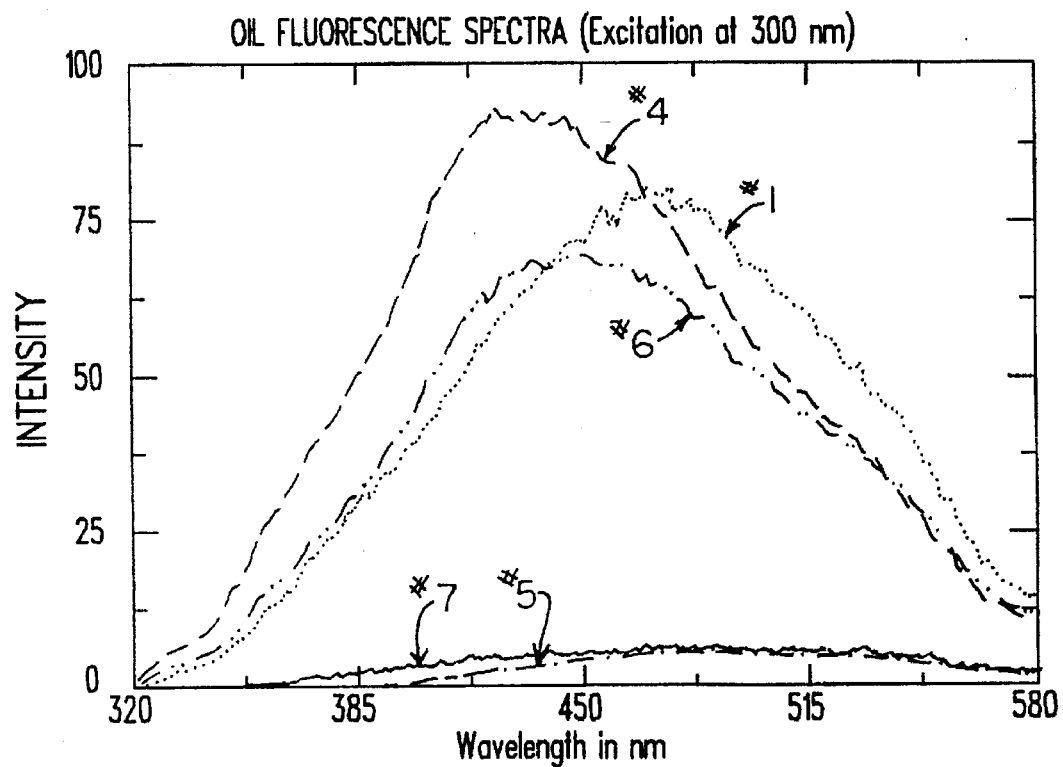
FIG. 8 is a graph comparing the emission spectra of FIGS. 7(a) through 7(e)
Figure 9:
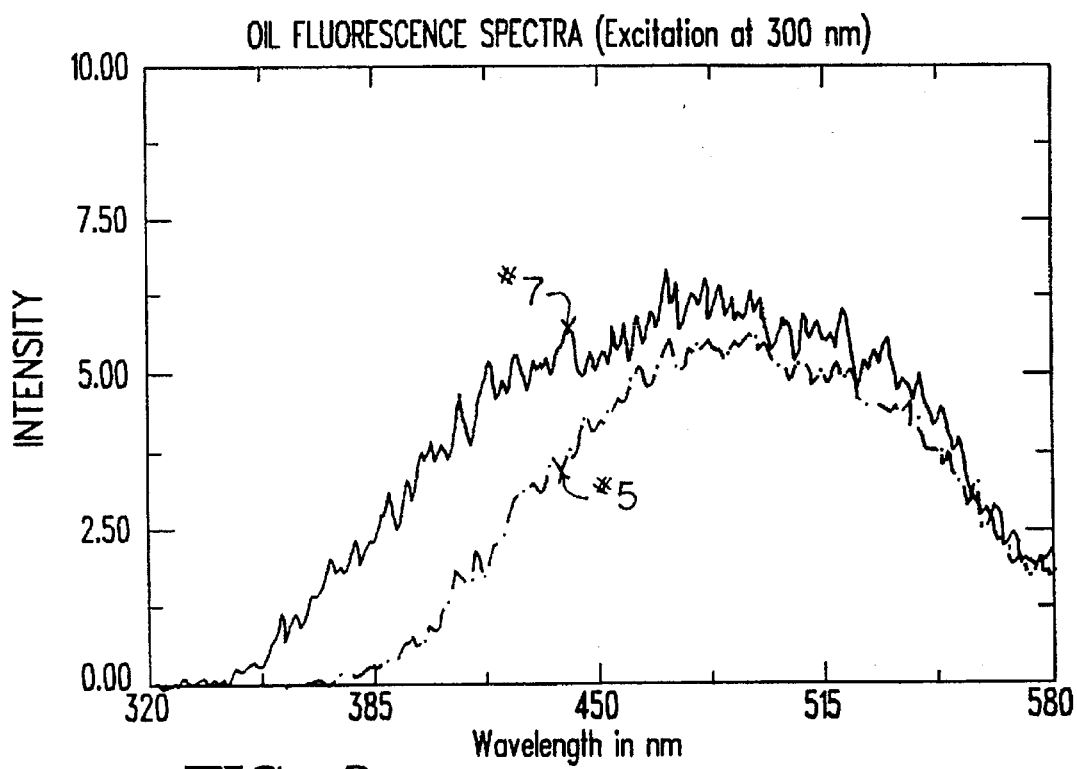
FIG. 9 is a graph distinguishing the emission spectra of FIGS. 7(b) and 7(d)
Figure 10A:
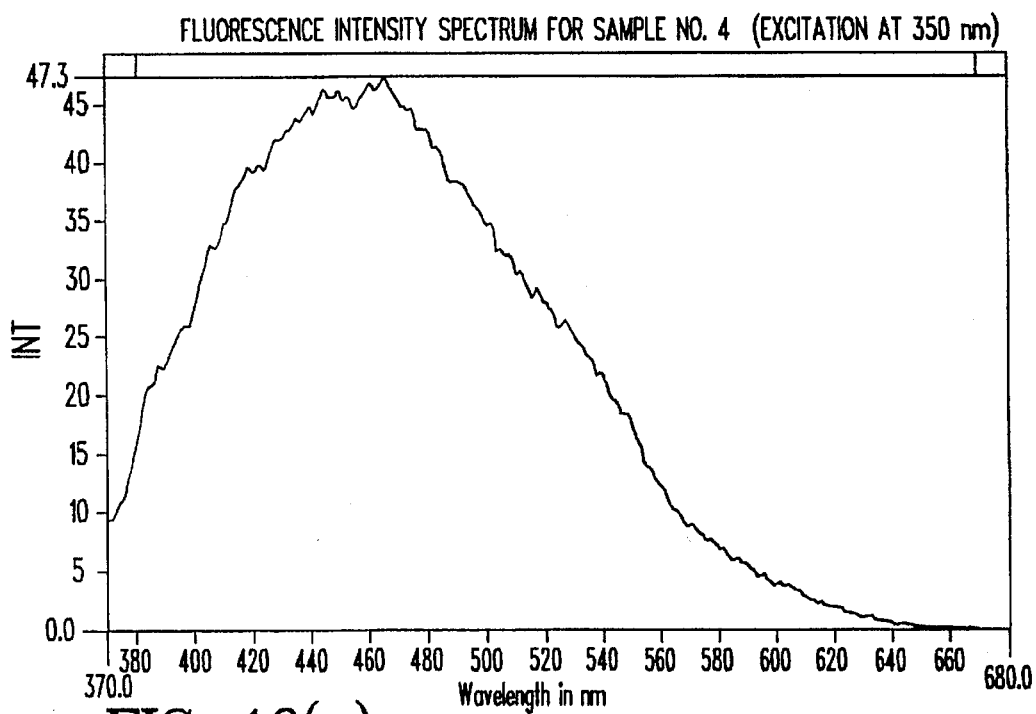
FIGS. 10(a) through 10(e) are graphs depicting the emission (i.e., fluorescence) spectra of the crude oil and crude oil component samples of FIGS. 7(a) through 7(e), respectively, excited at 350 nm.
Figure 10B:
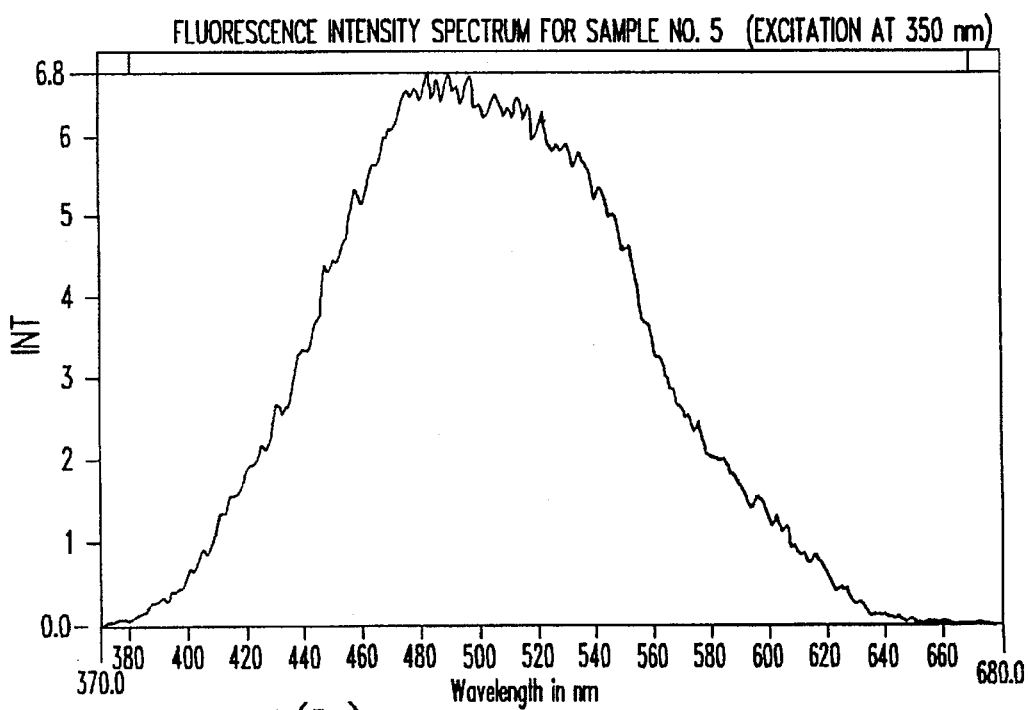
Figure 10C:
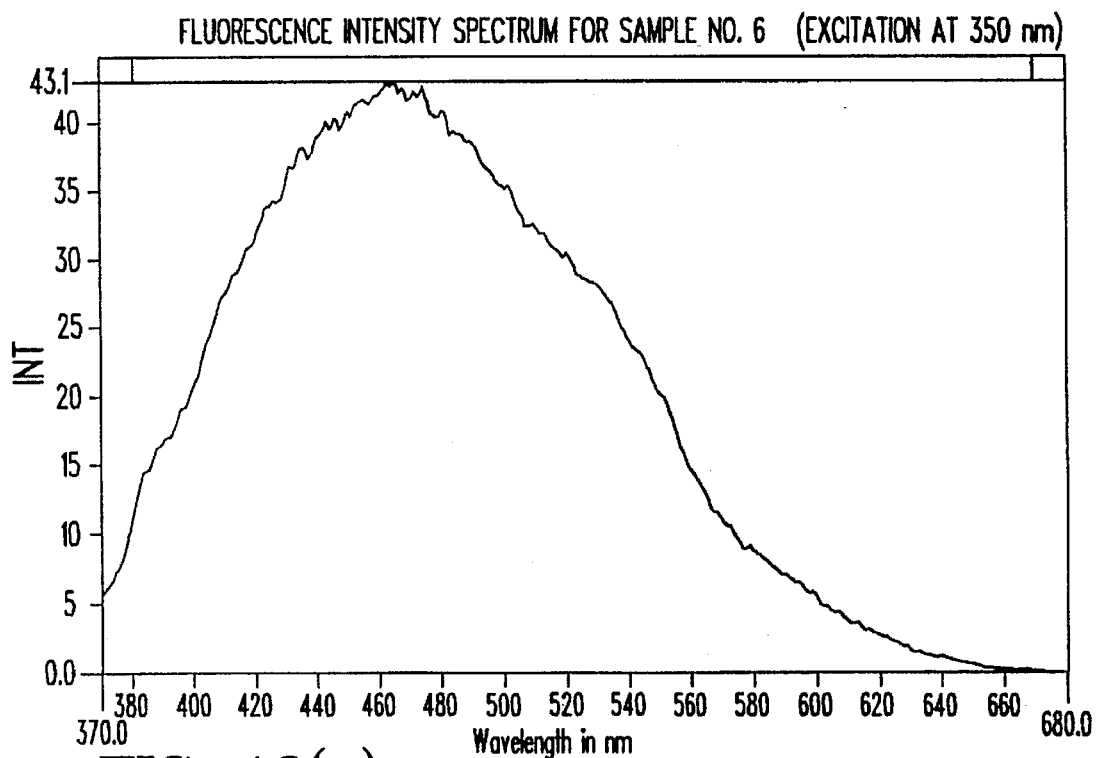
Figure 10D:
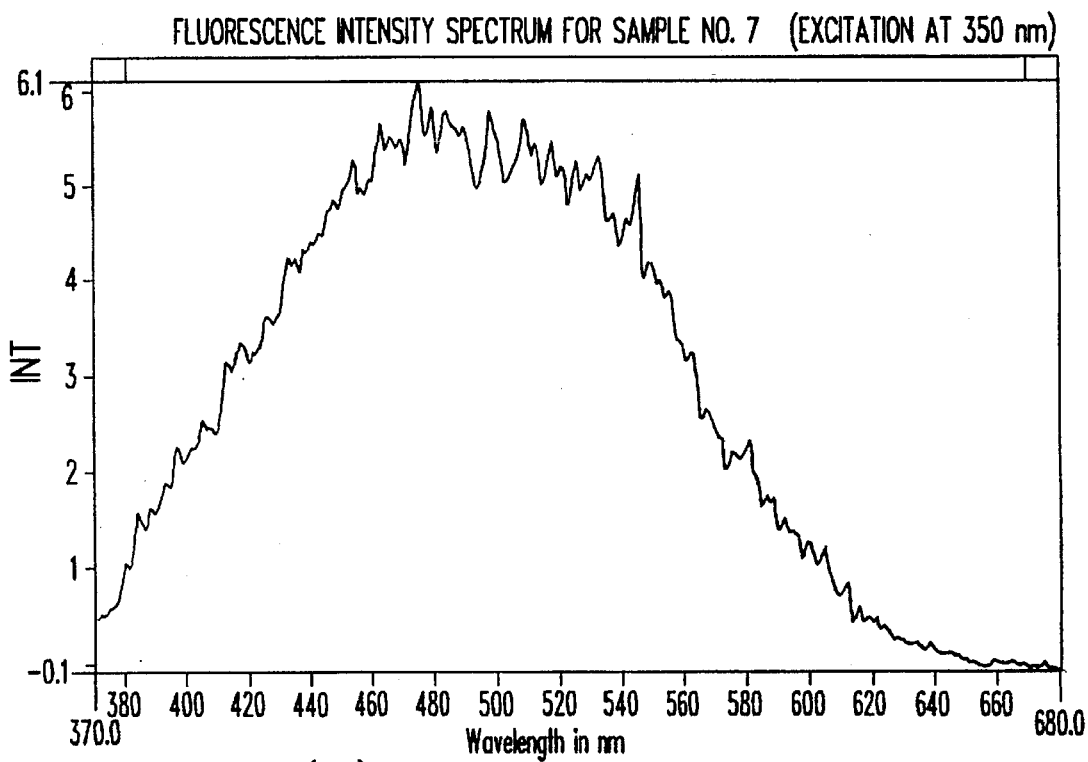
Figure 10E:
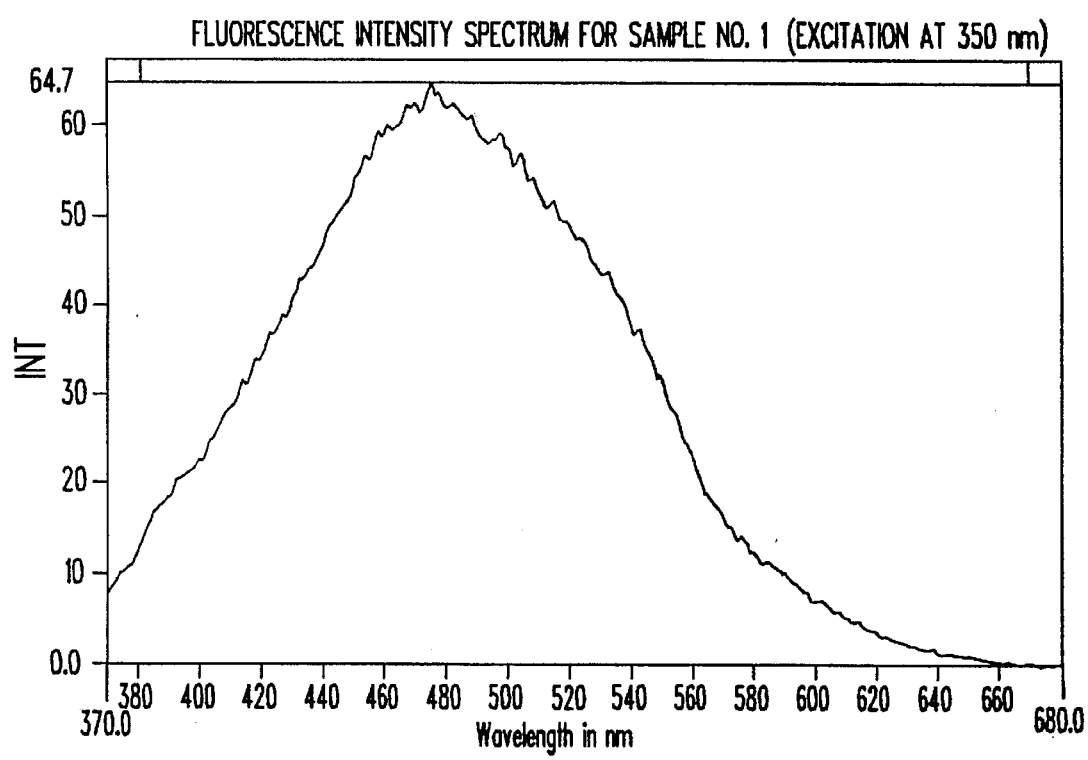
Figure 11A:
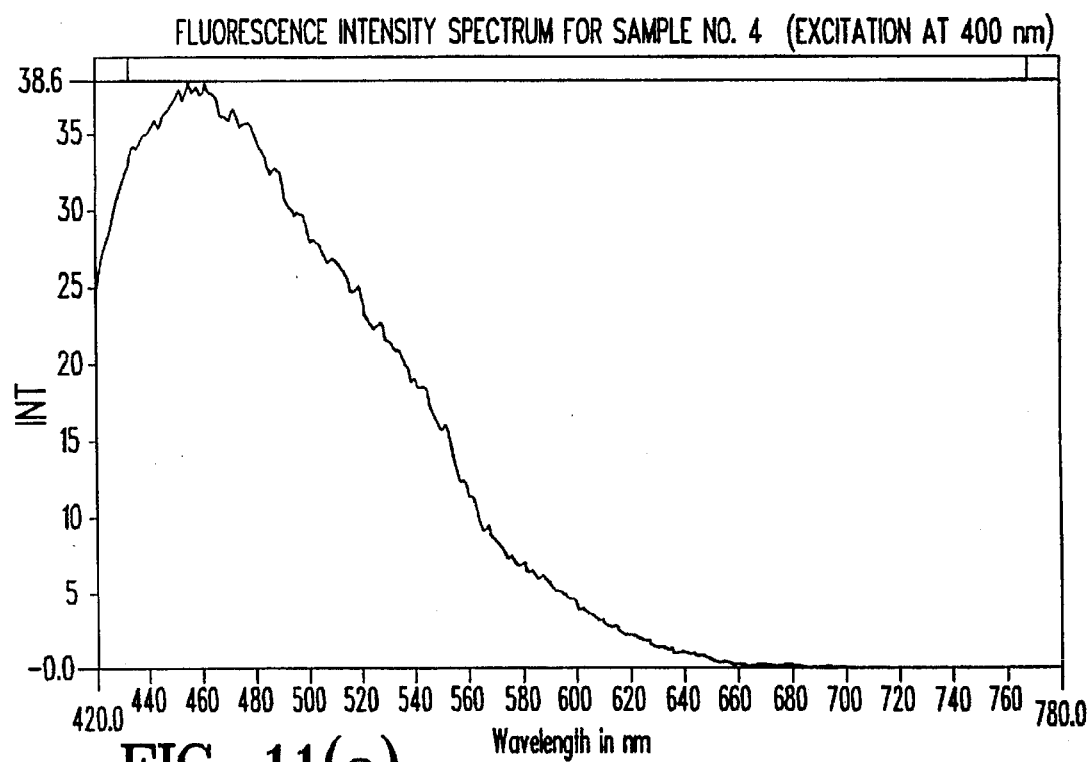
FIGS. 11(a) through 11(e) are graphs depicting the emission (i.e., fluorescence) spectra of the crude oil and crude oil component samples of FIGS. 7(a) through 7(e), respectively, excited at 400 nm.
Figure 11B:
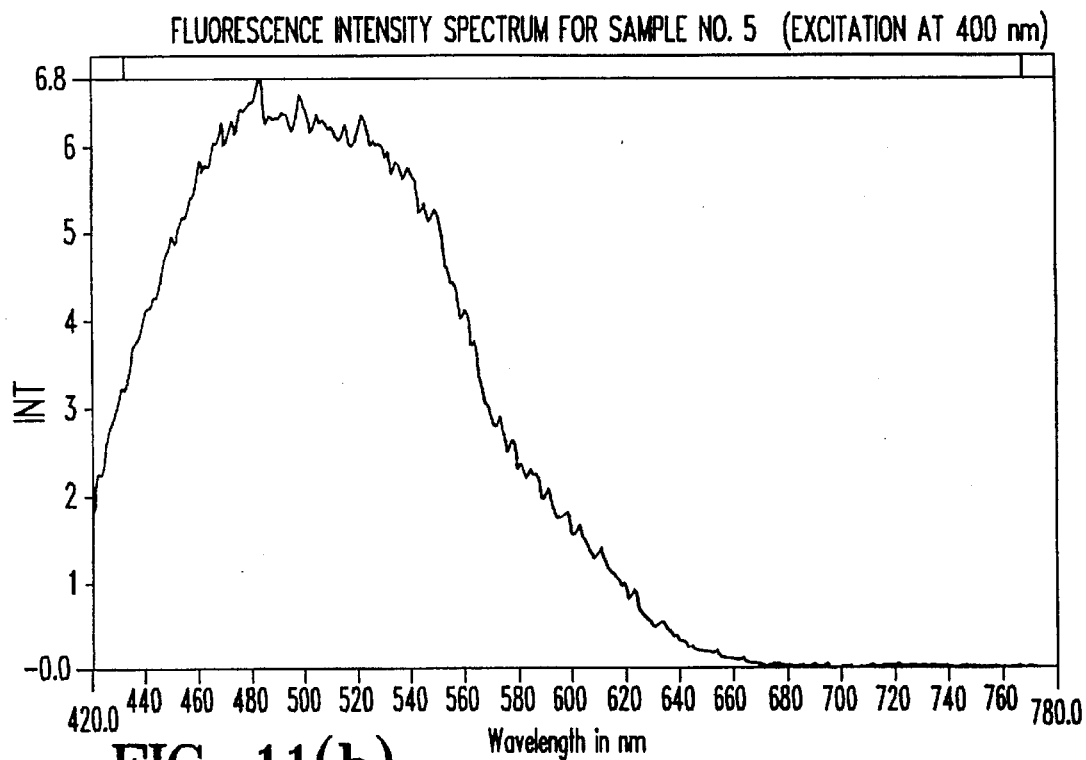
Figure 11C:
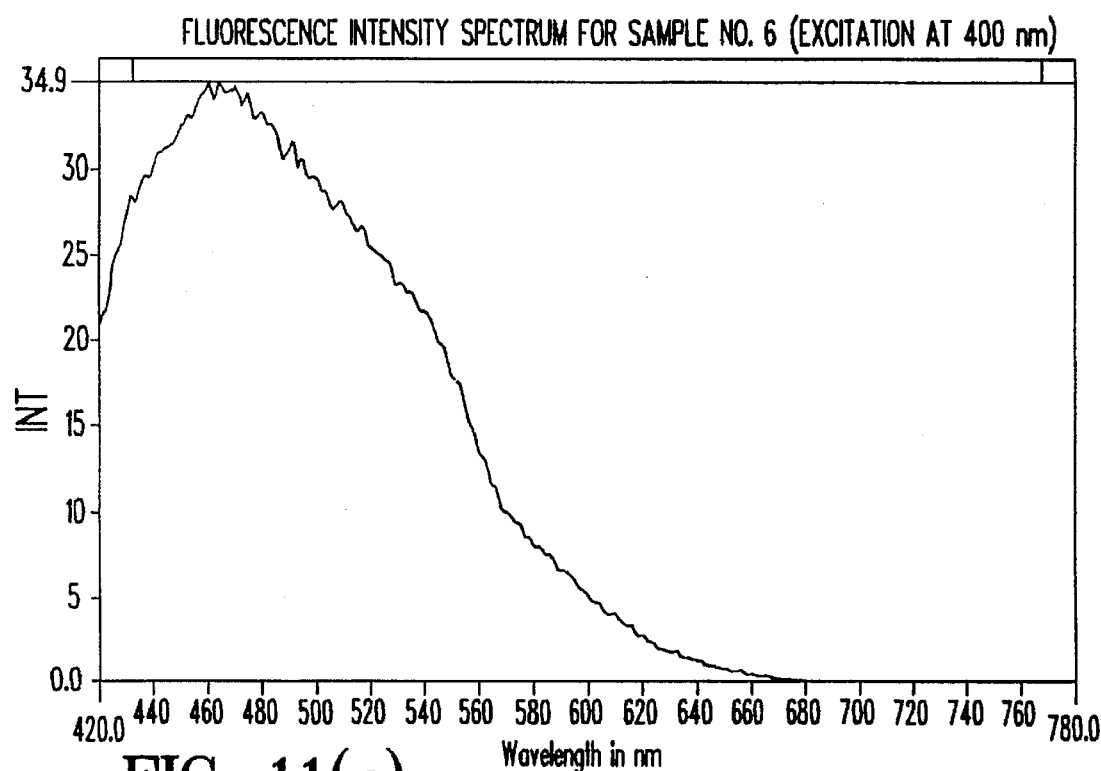
Figure 11D:
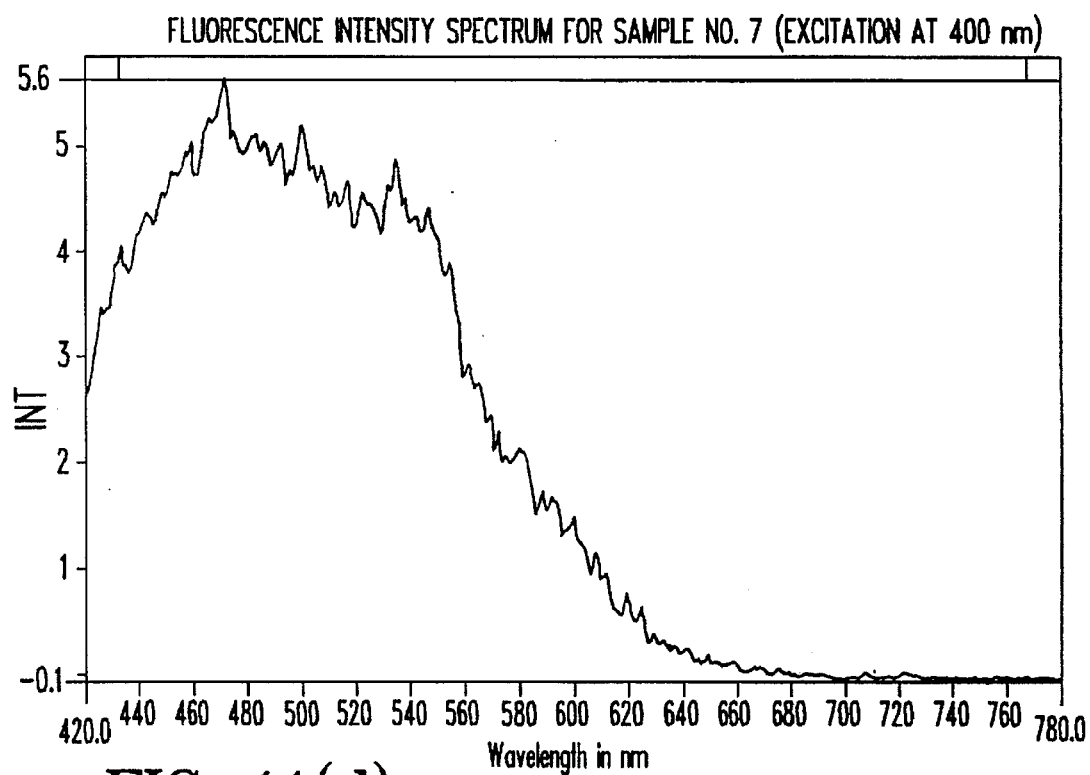
Figure 11E:
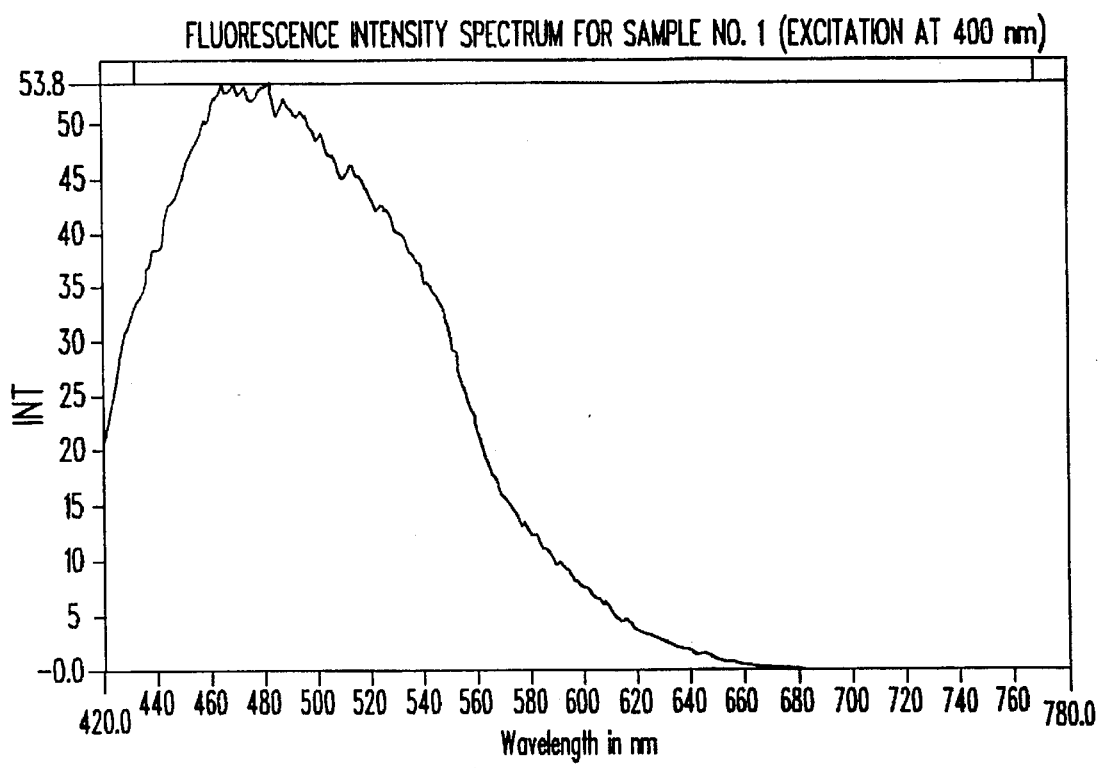
Figure 12A:
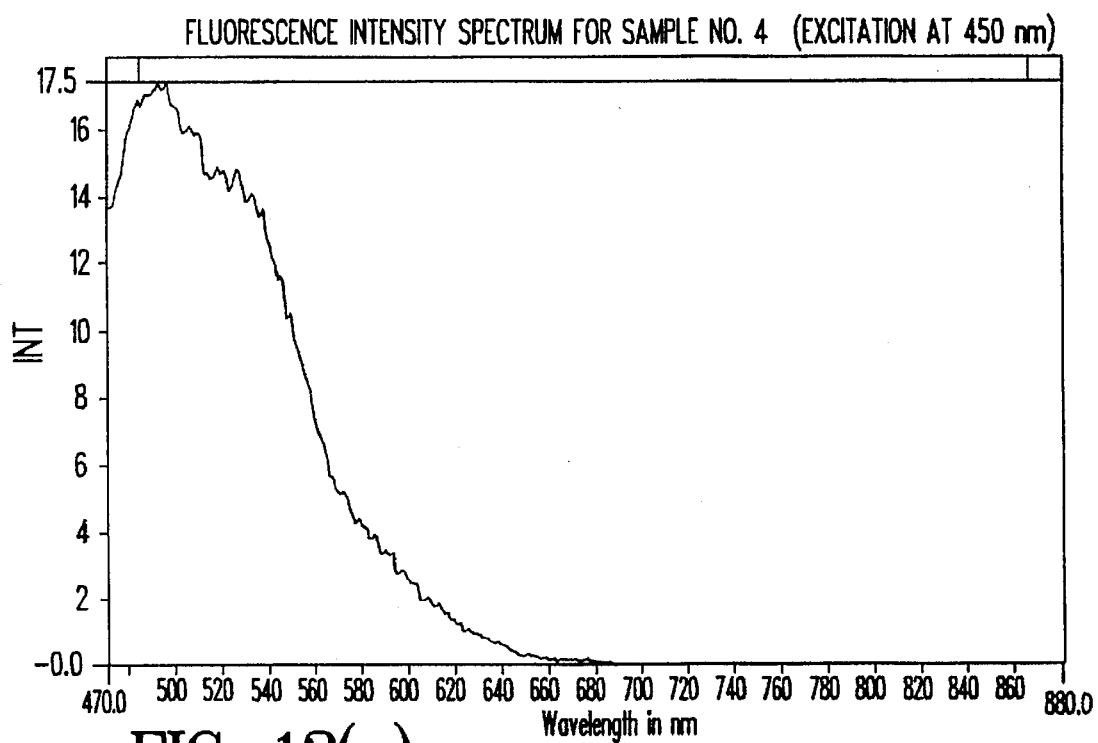
FIGS. 12(a) through 12(e) are graphs depicting the emission (i.e., fluorescence) spectra of the crude oil and crude oil component samples of FIGS. 7(a) through 7(e), respectively, excited at 450 nm.
Figure 12B:
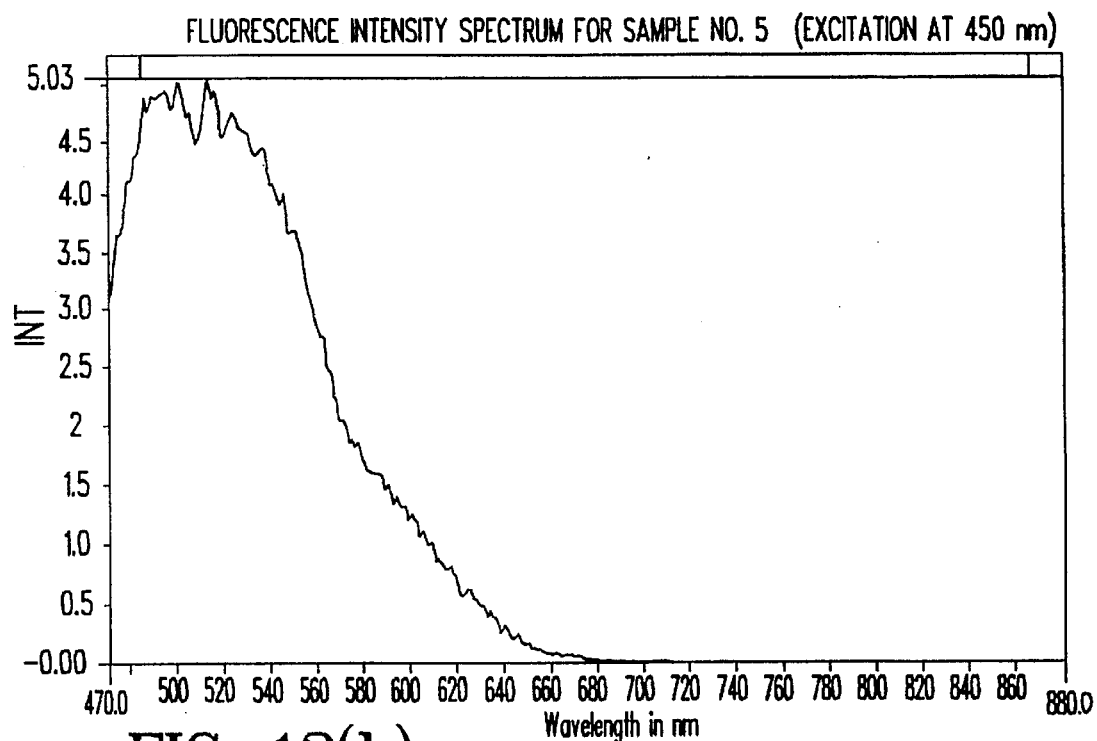
Figure 12C:
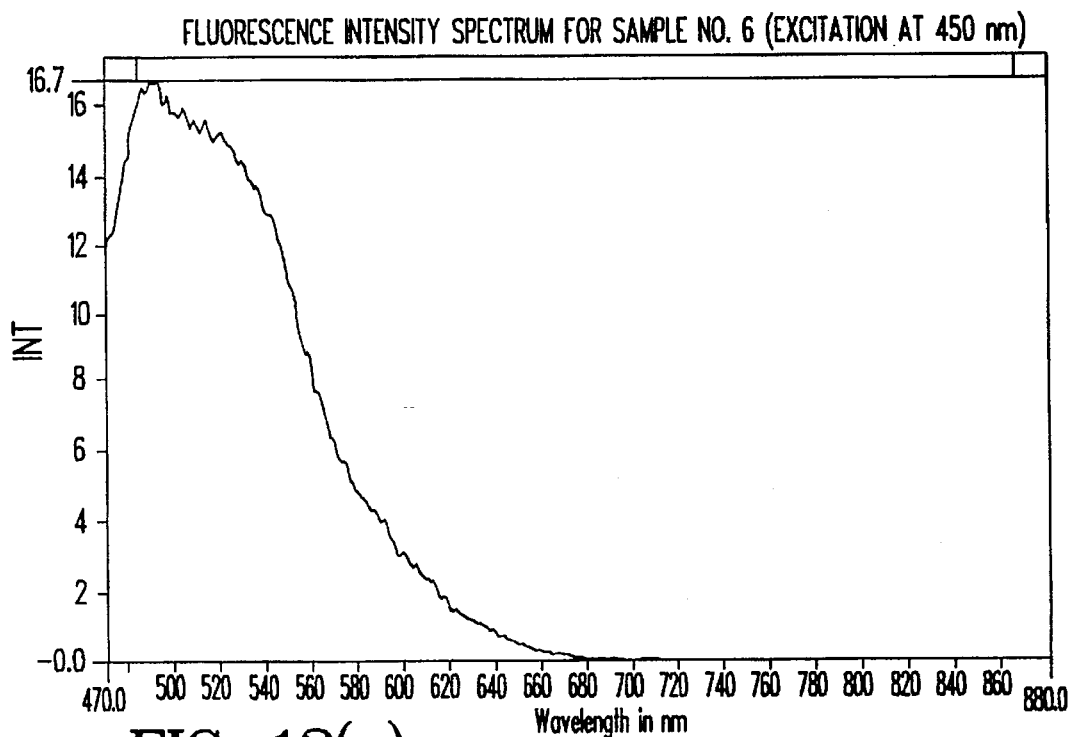
Figure 12D:
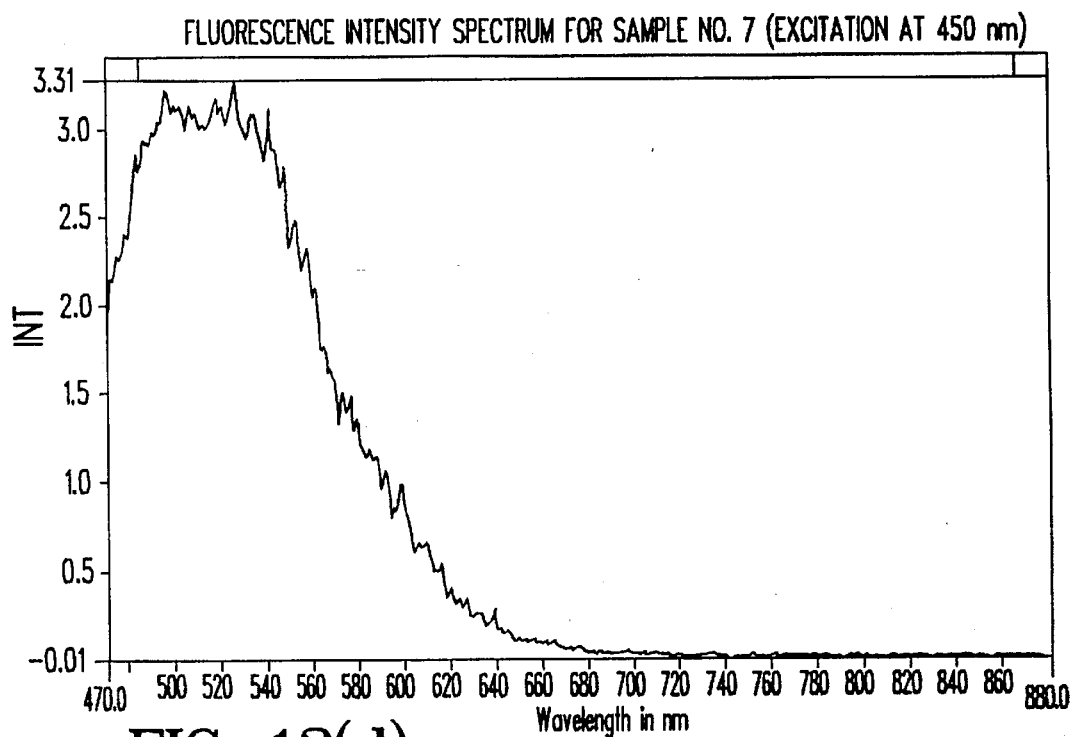
Figure 12E:
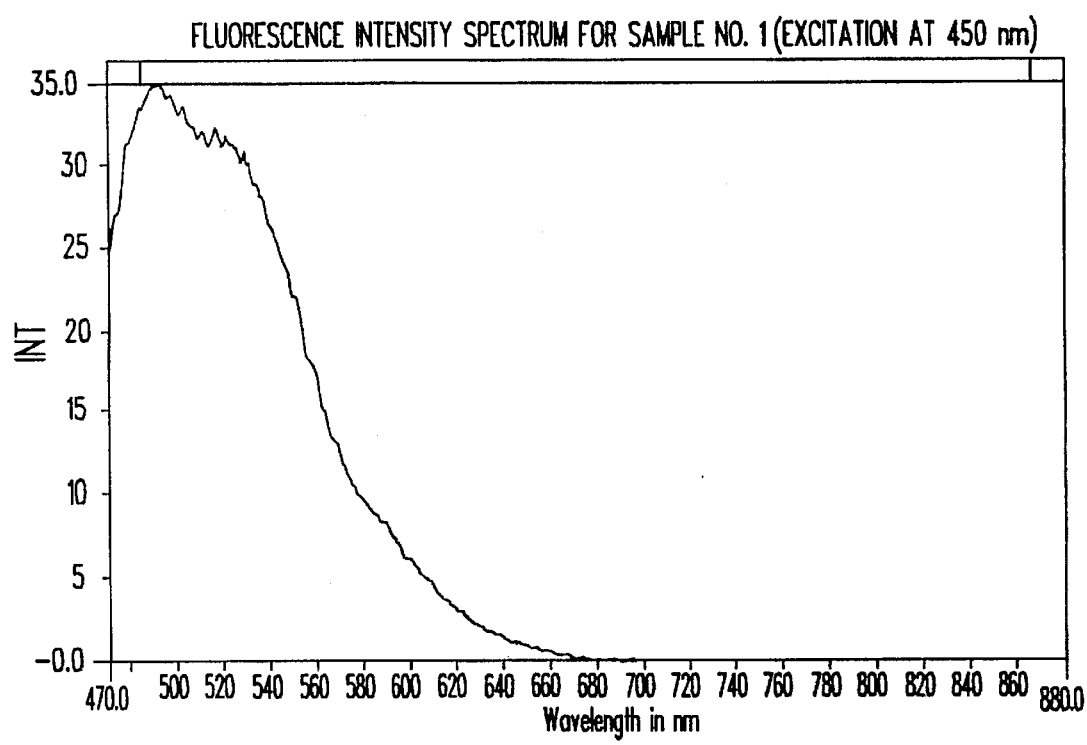
Figure 13A:
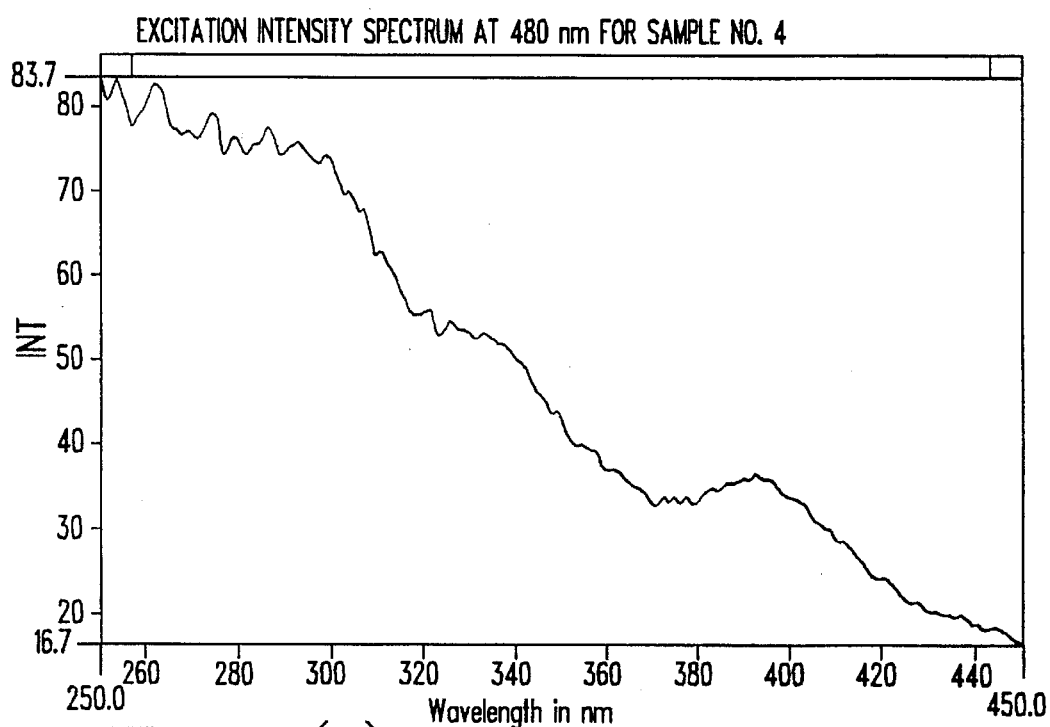
FIGS. 13(a) through 13(e) are graphs depicting the excitation spectra at 480 nm for the crude oil and crude oil component samples of FIGS. 7(a) through 7(e), respectively.
Figure 13B:
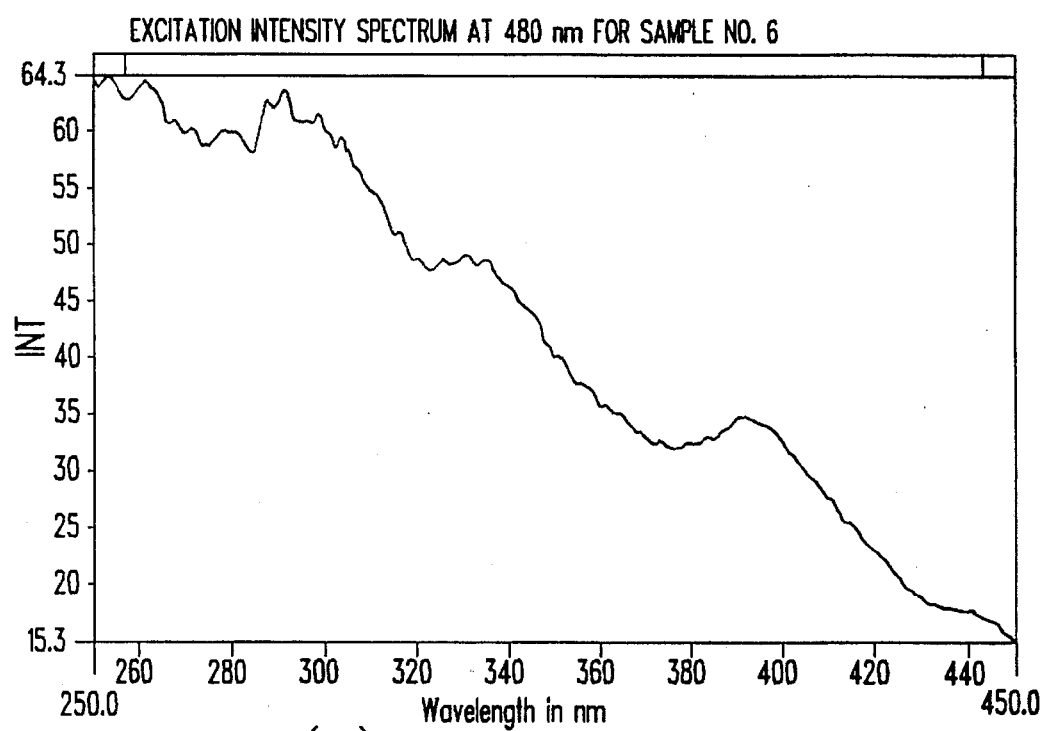
Figure 13C:
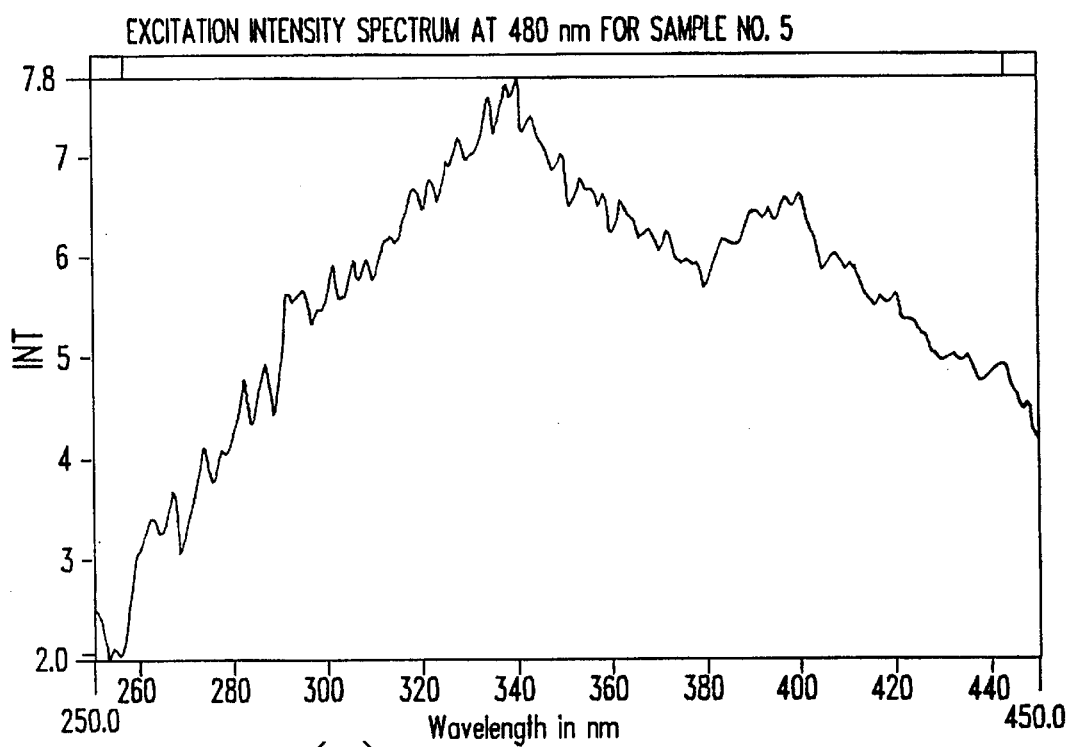
Figure 13D:
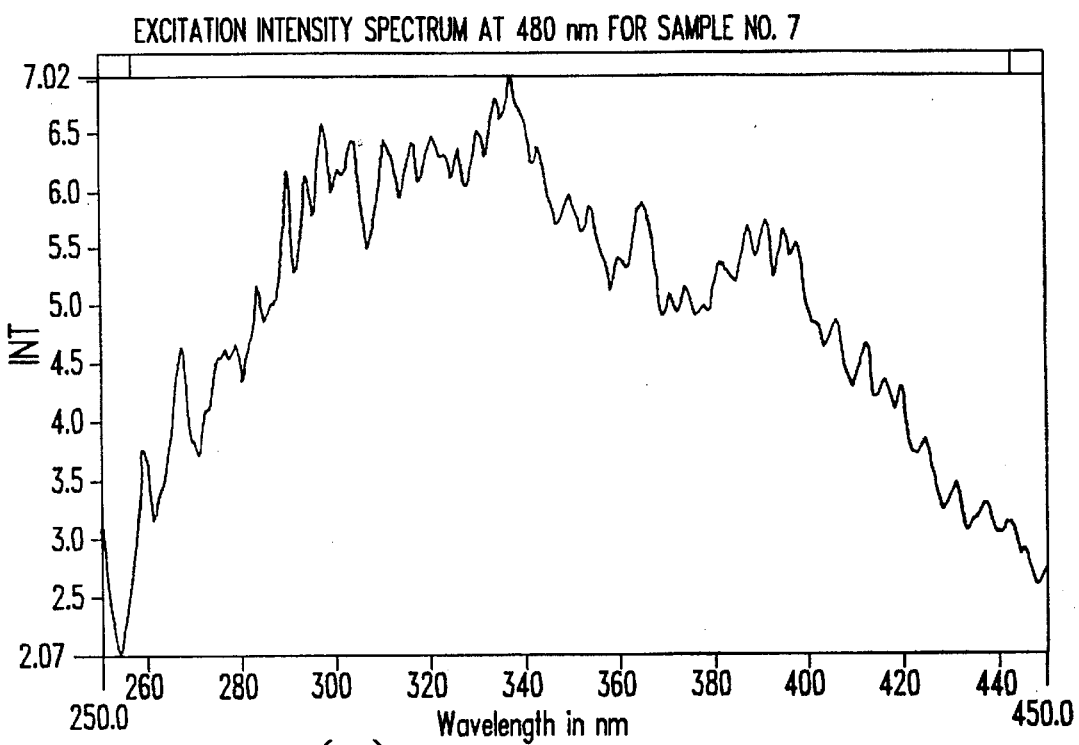
Figure 13E:
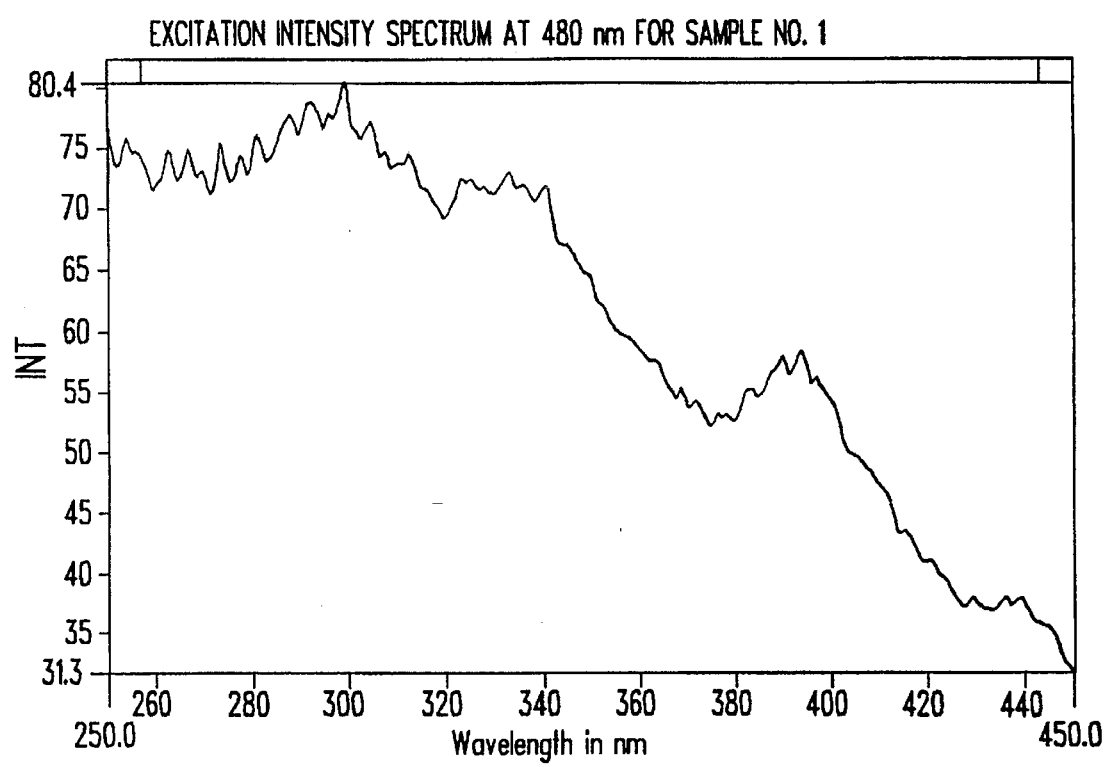

Referring now to FIGS. 7 and 10 through 12, there are shown the emission spectra for Sample Nos. 4, 5, 6, 7 and 1 at excitation wavelengths of 300 nm, 350 nm, 400 nm and 450 nm, respectively. FIG. 8 contrasts the emission spectra for Sample Nos. 4, 5, 6, 7 and 1 at an excitation wavelength of 300 nm, and FIG. 9 contrasts in greater detail the emission spectra for Sample Nos. 5 and 7 at an excitation wavelength of 300 nm. The excitation spectra for Sample Nos. 4, 5, 6, 7 and 1 at an emission wavelength of 480 nm are shown in FIGS. 13(a) through 13(e).

The spectral differences in fluorescence between the different types of samples are apparent from the drawings, the extent of the differences varying depending upon the wavelengths used. For example, larger spectral differences in the various profiles can be seen using excitation at 300 nm and 350 nm than at 400 nm and 450 nm. For 300 nm and 350 nm excitation, the spectra for Sample Nos. 4 and 6 are similar, with Sample No. 6 being broadened to red while Sample Nos. 5 and 7 are similar with Sample No. 7 being broadened to the blue side. Sample Nos. 4 and 6 are spectrally different from Sample Nos. 5 and 7. The difference becomes less for 400 nm and 450 nm excitation. As seen best in FIG. 9, the intensities for Sample Nos. 5 and 7 are smaller than for the other samples; nevertheless, the spectral profiles for Sample Nos. 5 and 7 are distinguishable. The asphaltene-containing Sample No. 5 seems to emit more in the red (450 to 600 nm range) while the paraffin-containing Sample No. 7 seems to emit more in the blue (320 to 420 nm range). Therefore, it would appear that the blue portion of the oil emission spectrum arises from organic paraffins while the red portion arises from asphaltenes. However, their contribution to the emission intensity for the entire oil spectrum would appear to be small (see FIG. 8).

The excitation spectra for the various types of samples are very different. Sample Nos. 4 and 6 have similar profiles while Sample Nos. 5 and 7 are similar to one another but different from Sample Nos. 4 and 6.

Figure 14:
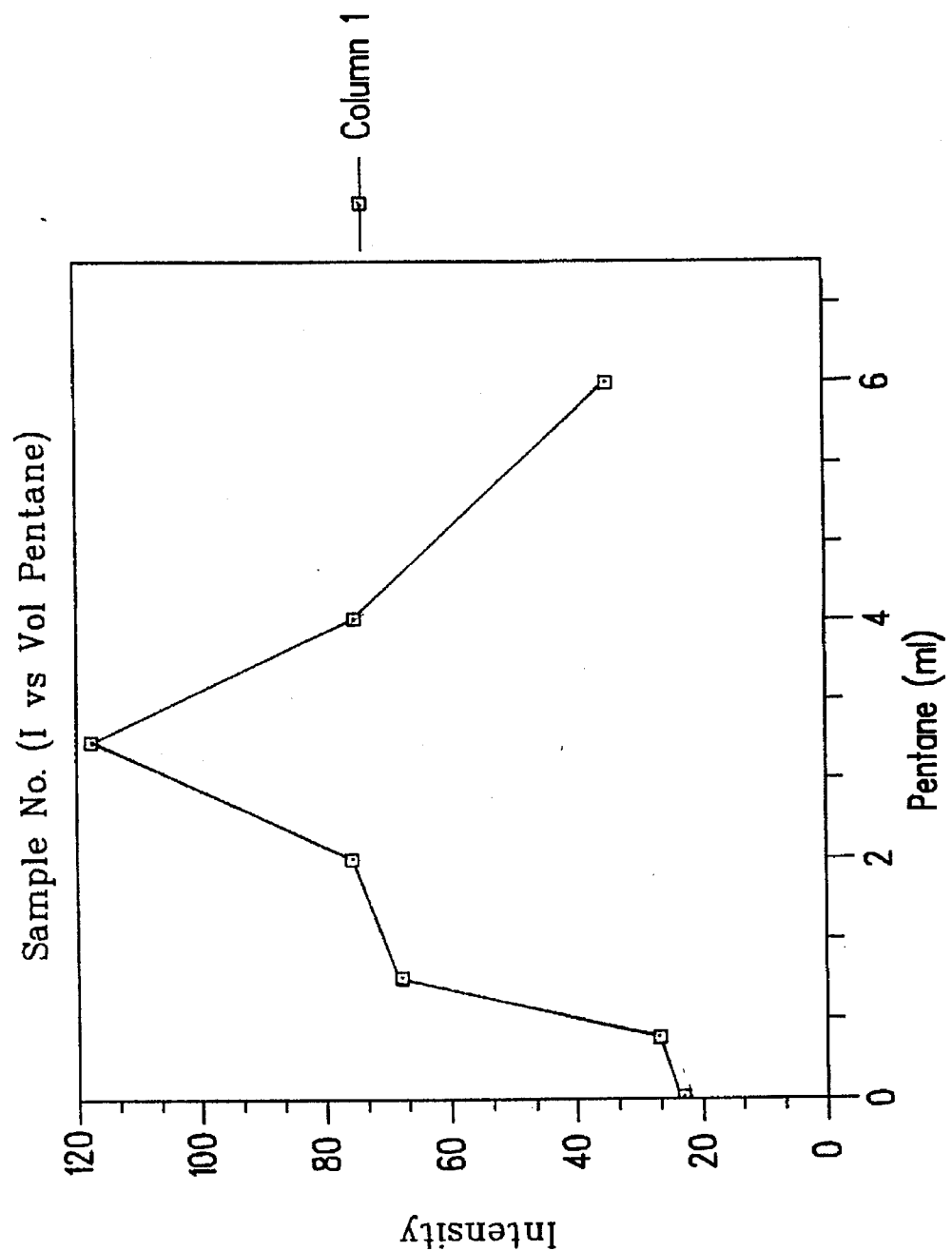
FIG. 14 is a graph depicting the fluorescence intensity of a crude oil sample as a function of pentane volume added thereto.

Referring now to FIG. 14 (see also curve #1 of FIG. 15), the fluorescence intensity of Sample No. 4 excited at 300 nm and measured at 440 nm is plotted against added pentane volume. As can be seen, the intensity peaks at a well-defined concentration, indicating the effect of asphaltene and paraffin precipitation.

Figure 15:
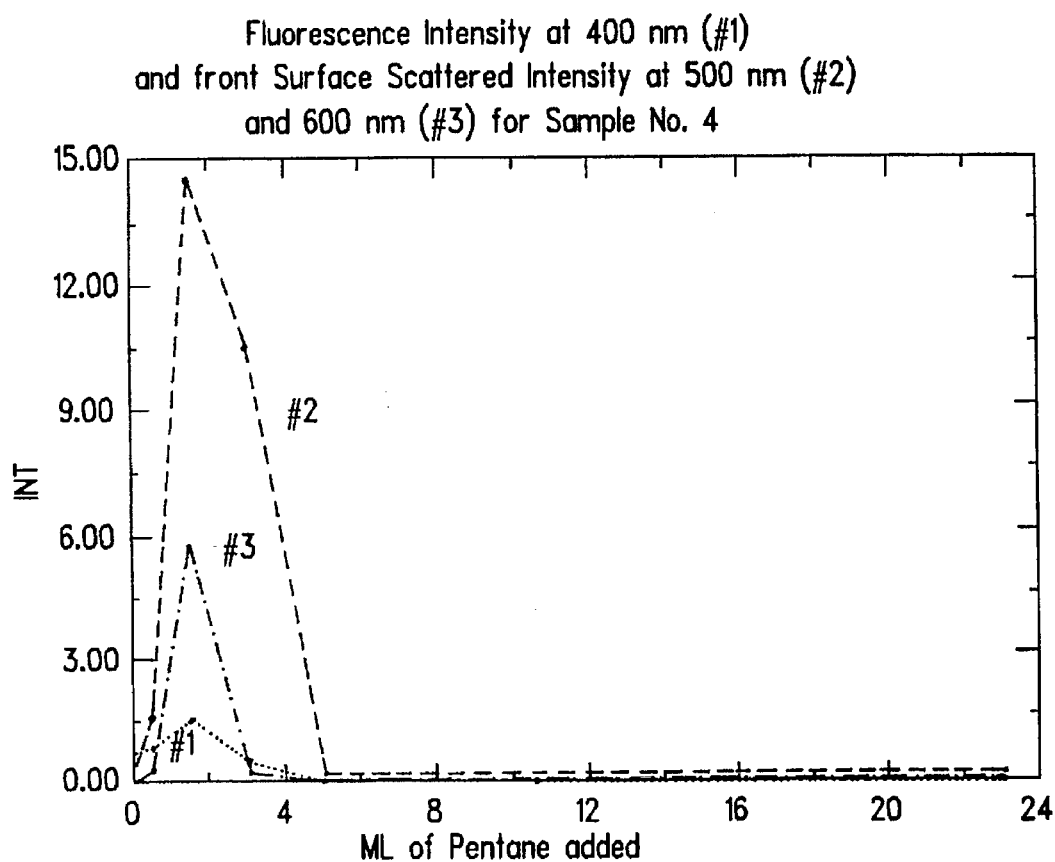
FIG. 15 is a graph depicting the fluorescence intensity at 400 nm, as well as the front surface intensity scattered at 500 nm and 600 nm, of a crude oil sample as a function of pentane concentration.

Referring now to FIG. 15, curves #2 and 3 represent the first surface scattering intensity at 500 nm and 600 nm, respectively, measured from Sample No. 4 at different concentrations of pentane. The solutions were prepared by mixing quantities of Sample No. 4 and pentane in a large container and then placing the mixture in a 1 mm cuvette for each concentration. The amount of oil for each solution was set at 1 ml and the amount of pentane was varied. As can be seen, curves #2 and 3 rise and peak near 1.5 to 2 ml of pentane and then decrease beyond 3 ml of pentane. The changes in intensity range from 50 to 1300 times. The critical enhancement region is sharp with pentane concentration. These methods clearly show that critical phase transitions in oils can be detected by optical methods.

Figure 16:
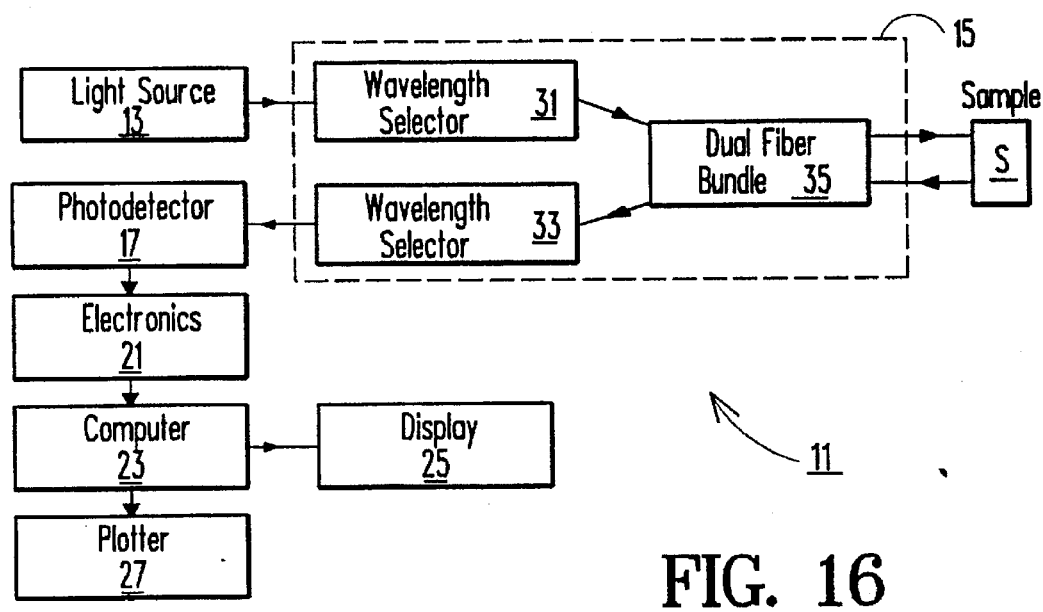
FIG. 16 is a block diagram of one embodiment of an apparatus for evaluating the composition of an oil sample using optical spectroscopy, the apparatus being constructed according to the teachings of the present invention.

Referring now to FIG. 16, there is shown a block diagram of an apparatus constructed according to the teachings of the present invention for evaluating the composition of an oil sample using optical spectroscopy, the apparatus being represented generally by reference numeral 11.

Apparatus 11 includes a light source 13, a fiber assembly 15 for delivering light from light source 13 to a sample S and for collecting light therefrom, a photodector 17 for measuring the collected light and transmitting corresponding electrical signals, electronics 21 and a computer 23 for processing the transmitted electrical signals, and a display 25 and plotter 27 for displaying the output of computer 23.

Figure 17:
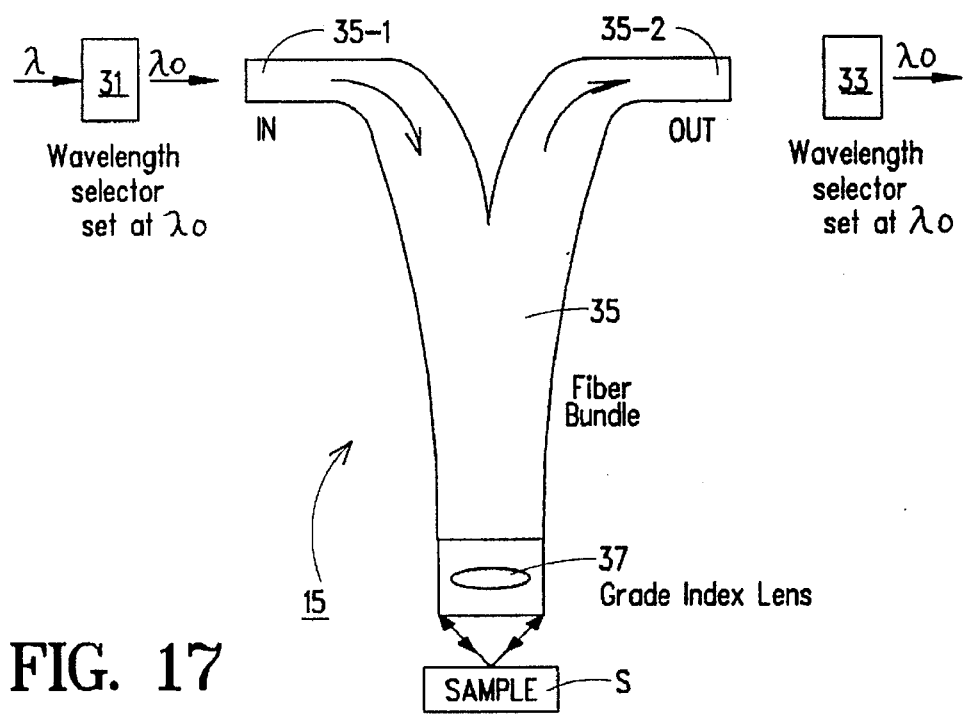
FIG. 17 is a schematic diagram of the fiber assembly of the apparatus shown in FIG. 16.

Fiber assembly 15 includes a first wavelength filter or selector 31, a second wavelength filter or selector 33 and a fiber bundle 35. As seen best in FIG. 17, fiber bundle 35 is bifurcated at one end into an input end 35-1 and an output end 35-2. The opposite end of fiber bundle 35 is not bifurcated and is provided with a grade index lens 37 or the like for focusing light onto the sample and collecting light from the sample. Wavelength selector 31, which only passes light at wavelength $\lambda_0$, is positioned in front of input end 35-1 of fiber bundle 35, and wavelength selector 33, which also only passes light at wavelength $\lambda_0$, is positioned behind output end 35-2 of fiber bundle 35. Because wavelength selectors 31 and 33 are selective for the same wavelength, apparatus 11 is well-suited evaluations based on light-scattering measurements.

Figure 18A:
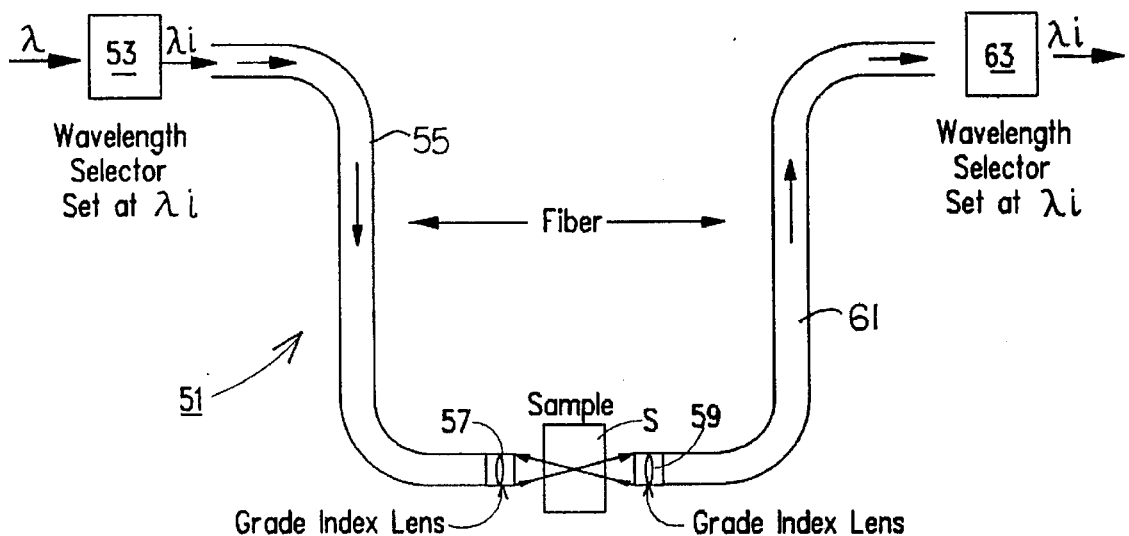
FIGS. 18(a) and 18(b) are schematic diagrams of alternative fiber assemblies adapted for use in the apparatus of FIG. 16.
Figure 18B:
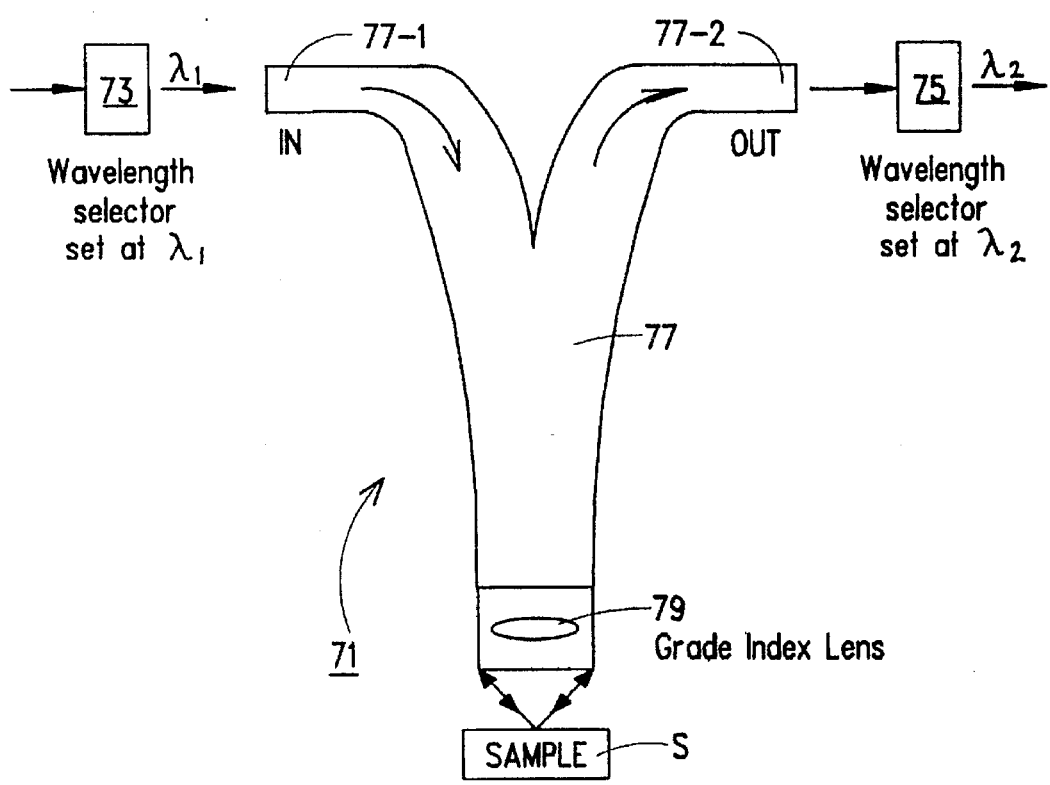

Referring now to FIGS. 18(a) and 18(b), there are shown schematic diagrams of alternative fiber assemblies 51 and 71, respectively, which may be substituted for fiber assembly 15 for use with the remaining components of apparatus 11. Fiber assembly 51, which is particularly well-suited for absorption measurements, includes a first wavelength selector 53 for selectively passing light at wavelength $\lambda_i$, a first fiber bundle 55 positioned behind wavelength selector 53, a first grade index lens 57 positioned at the output end of bundle 55 for focusing light onto a sample S, a second grade index lens 59 for collecting light from the opposite side of sample S, a second fiber bundle 61 positioned behind lens 59 and a second wavelength selector 63 selective for light of wavelength $\lambda_i$ positioned at the output end of fiber bundle 61.

Fiber assembly 71, which is particularly well-suited for fluorescence measurements, includes a first wavelength selector 73, a second wavelength filter or selector 75 and a fiber bundle 77. One end of bundle 77 is bifurcated into an input end 77-1 and an output end 77-2. The opposite end of fiber bundle 35 is not bifurcated and is provided with a grade index lens 79 or the like for focusing light onto the sample S and collecting light from the sample. Wavelength selector 73, which only passes light at an excitation wavelength $\lambda_i$, is positioned in front of input end 77-1 of fiber bundle 77, and wavelength selector 75, which only passes light at an emission wavelength $\lambda_2$, is positioned behind output end 77-2 of fiber bundle 77.

As can readily be appreciated, by making the fiber bundles of fiber assemblies 15, 51 and 71 sufficiently long, the apparatus of the present invention can be used to test oil samples located at a remote location, for example, at a drilling site.

Some of the attributes, features, advantages and applications of the present invention are as follows: Using optical spectroscopy, one can determine the quality and purity of an oil sample; determine the existence of certain components in an oil sample (e.g. asphaltenes and/or paraffins); determine the presence of precipitates in an oil sample; determine the presence of organic deposits (paraffins) in oil transfer tubes or pipes, tanks and drilling tubes; detect the presence of oil during the drilling of a well; note the effects on an oil sample by dilution of the sample with various solvents; detect oil seepage; determine if oil media or oil polymer media are ionized or ion complexing with and without the addition of organic dyes; determine the optimum mixing time and structure of cationic crosslinked organic polymer gels in aqueous media used in enhanced oil recovery from oil wells.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method for evaluating the composition of an oil sample, said method comprising the steps of:

(a) exciting the oil sample with light of an appropriate excitation wavelength, said appropriate excitation wavelength being about 300 nm, and observing the resultant fluorescence spectrum from about 320 nm to about 580 nm for the oil sample; and (b) comparing the resultant fluorescence spectrum from the oil sample to appropriate standards derived from known components of crude oil.

\* \* \* \* \*